United States Patent
O'Dell et al.

(10) Patent No.: US 9,464,992 B2
(45) Date of Patent: *Oct. 11, 2016

(54) AUTOMATED WAFER DEFECT INSPECTION SYSTEM AND A PROCESS OF PERFORMING SUCH INSPECTION

(71) Applicant: Rudolph Technologies, Inc., Flanders, NJ (US)

(72) Inventors: Jeffrey L. O'Dell, Deephaven, MN (US); Thomas Verburgt, Eden Prairie, MN (US); Mark Harless, New Hope, MN (US); Cory Watkins, Ramsey, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/093,130

(22) Filed: Apr. 7, 2016

(65) Prior Publication Data

US 2016/0223470 A1 Aug. 4, 2016

Related U.S. Application Data

(63) Continuation of application No. 12/789,829, filed on May 28, 2010, now Pat. No. 9,337,071, which is a continuation of application No. 10/915,666, filed on Aug. 10, 2004, now Pat. No. 7,729,528, which is a (Continued)

(51) Int. Cl.
*G06K 9/00* (2006.01)
*G01N 21/95* (2006.01)
(Continued)

(52) U.S. Cl.
CPC ...... *G01N 21/9501* (2013.01); *G01N 21/8803* (2013.01); *G01N 21/8806* (2013.01); *G06T 7/0004* (2013.01); *H04N 5/2256* (2013.01);
(Continued)

(58) Field of Classification Search
USPC .......................................... 382/145
See application file for complete search history.

(56) References Cited

U.S. PATENT DOCUMENTS 3,963,354 A 6/1976 Feldman et al.
4,037,941 A 7/1977 Belleson et al.
(Continued)

FOREIGN PATENT DOCUMENTS

GB 1532901 11/1978
JP 51137379 11/1976
(Continued)

OTHER PUBLICATIONS

*August Technology Corporation v. Camtek Ltd.*, Transcript of Steven Palm Deposition dated Jan. 5, 2007; 49 pages.
(Continued)

*Primary Examiner* — John Strege
(74) *Attorney, Agent, or Firm* — Merchant & Gould P.C.

(57) ABSTRACT

An automated defect inspection system has been invented and is used on patterned wafers, whole wafers, broken wafers, partial wafers, sawn wafers such as on film frames, JEDEC trays, Auer boats, die in gel or waffle packs, MCMs, etc., and is specifically intended and designed for second optical wafer inspection for such defects as metalization defects (such as scratches, voids, corrosion, and bridging), diffusion defects, passivation layer defects, scribing defects, glassivation defects, chips and cracks from sawing, solder bump defects, and bond pad area defects.

11 Claims, 19 Drawing Sheets

Related U.S. Application Data continuation of application No. 09/562,273, filed on Apr. 29, 2000, now Pat. No. 6,826,298, which is a continuation of application No. 09/352,564, filed on Jul. 13, 1999, now Pat. No. 6,324,298.

(60) Provisional application No. 60/092,923, filed on Jul. 15, 1998, provisional application No. 60/092,701, filed on Jul. 14, 1998.

(51) Int. Cl.
    *G01N 21/88*     (2006.01)
    *G06T 7/00*     (2006.01)
    *H04N 5/225*     (2006.01)

(52) U.S. Cl.
    CPC .......... *G01N 2021/8838* (2013.01); *G01N 2201/0696* (2013.01); *G01N 2201/0697* (2013.01); *G01N 2201/06113* (2013.01); *G01N 2201/12* (2013.01); *G06T 2207/30148* (2013.01)

(56) References Cited

U.S. PATENT DOCUMENTS

| | | |
|---|---|---|
| 4,131,803 A | 12/1978 | Takematsu et al. |
| 4,136,930 A | 1/1979 | Gomm et al. |
| 4,143,770 A | 3/1979 | Grimmell et al. |
| 4,146,135 A | 3/1979 | Sarkar et al. |
| 4,148,065 A | 4/1979 | Nakagawa et al. |
| 4,162,126 A | 7/1979 | Nakagawa et al. |
| 4,185,298 A | 1/1980 | Billet et al. |
| 4,209,257 A | 6/1980 | Uchiyama et al. |
| 4,223,346 A | 9/1980 | Neiheisel et al. |
| 4,240,750 A | 12/1980 | Kurtz et al. |
| 4,246,098 A | 1/1981 | Conway et al. |
| 4,247,203 A | 1/1981 | Levy et al. |
| 4,284,357 A | 8/1981 | Kudo |
| 4,311,427 A | 1/1982 | Coad et al. |
| 4,328,553 A | 5/1982 | Fredriksen et al. |
| 4,376,583 A | 3/1983 | Alford et al. |
| 4,377,340 A | 3/1983 | Green et al. |
| 4,378,159 A | 3/1983 | Galbraith |
| 4,464,705 A | 8/1984 | Horowitz |
| 4,500,202 A | 2/1985 | Smyth |
| 4,513,316 A | 4/1985 | Kobayashi et al. |
| 4,527,070 A | 7/1985 | Matsui et al. |
| 4,532,650 A | 7/1985 | Wihl et al. |
| 4,542,404 A | 9/1985 | Duschl |
| 4,556,317 A | 12/1985 | Sandland et al. |
| 4,578,810 A | 3/1986 | MacFarlane et al. |
| 4,601,577 A | 7/1986 | Gotou et al. |
| 4,618,938 A | 10/1986 | Sandland et al. |
| 4,626,101 A | 12/1986 | Ogawa et al. |
| 4,639,587 A | 1/1987 | Chadwick et al. |
| 4,641,966 A | 2/1987 | Lemmers et al. |
| 4,644,172 A | 2/1987 | Sandland et al. |
| 4,648,053 A | 3/1987 | Fridge |
| 4,659,220 A | 4/1987 | Bronte et al. |
| 4,691,231 A | 9/1987 | Fitzmorris et al. |
| 4,695,215 A | 9/1987 | Jacoby et al. |
| 4,731,855 A | 3/1988 | Suda et al. |
| 4,740,708 A | 4/1988 | Batchelder |
| 4,764,969 A | 8/1988 | Ohtombe et al. |
| 4,776,022 A | 10/1988 | Fox et al. |
| 4,799,175 A | 1/1989 | Sano et al. |
| 4,805,123 A | 2/1989 | Specht et al. |
| 4,806,774 A | 2/1989 | Lin et al. |
| 4,812,664 A | 3/1989 | Borden |
| 4,816,116 A | 3/1989 | Davis et al. |
| 4,816,686 A | 3/1989 | Hara et al. |
| 4,818,110 A | 4/1989 | Davidson |
| 4,820,932 A | 4/1989 | Miller |
| 4,823,394 A | 4/1989 | Berkin et al. |
| 4,845,558 A | 7/1989 | Tsai et al. |
| 4,859,863 A | 8/1989 | Schrader et al. |
| 4,877,326 A | 10/1989 | Chadwick et al. |
| 4,898,471 A | 2/1990 | Vaught et al. |
| 4,926,489 A | 5/1990 | Danielson et al. |
| 4,942,618 A | 7/1990 | Sumi et al. |
| 4,969,198 A | 11/1990 | Batchelder et al. |
| 4,992,949 A | 2/1991 | Arden |
| 5,030,008 A | 7/1991 | Scott et al. |
| 5,032,734 A | 7/1991 | Orazio, Jr. et al. |
| 5,058,178 A | 10/1991 | Ray |
| 5,076,692 A | 12/1991 | Neukermans et al. |
| 5,085,517 A | 2/1992 | Chadwick et al. |
| 5,091,963 A | 2/1992 | Litt et al. |
| 5,095,204 A | 3/1992 | Novini |
| 5,105,147 A | 4/1992 | Karasikov et al. |
| 5,120,126 A | 6/1992 | Wertz et al. |
| 5,127,726 A | 7/1992 | Moran |
| 5,131,755 A | 7/1992 | Chadwick et al. |
| 5,153,668 A | 10/1992 | Katzir et al. |
| 5,177,559 A | 1/1993 | Batchelder et al. |
| 5,195,171 A | 3/1993 | Takatori et al. |
| 5,245,671 A | 9/1993 | Kobayashi et al. |
| 5,274,434 A | 12/1993 | Morioka et al. |
| 5,276,498 A | 1/1994 | Galbraith et al. |
| 5,293,538 A | 3/1994 | Iwata et al. |
| 5,298,963 A | 3/1994 | Moriya et al. |
| 5,311,598 A | 5/1994 | Bose et al. |
| 5,355,212 A | 10/1994 | Wells et al. |
| 5,440,648 A | 8/1995 | Roberts et al. |
| 5,446,584 A | 8/1995 | Bacchi et al. |
| 5,455,870 A | 10/1995 | Sepai et al. |
| 5,457,490 A | 10/1995 | Doane |
| 5,497,381 A | 3/1996 | O'Donoghue et al. |
| 5,506,676 A | 4/1996 | Hendler et al. |
| 5,513,275 A | 4/1996 | Khalaj et al. |
| 5,517,234 A | 5/1996 | Gerber et al. |
| 5,537,669 A | 7/1996 | Evans et al. |
| 5,544,256 A | 8/1996 | Brecher et al. |
| 5,572,256 A | 11/1996 | Egawa et al. |
| 5,586,058 A | 12/1996 | Aloni et al. |
| 5,604,585 A | 2/1997 | Johnson et al. |
| 5,619,429 A | 4/1997 | Aloni et al. |
| 5,640,200 A | 6/1997 | Michael |
| 5,641,960 A | 6/1997 | Okubo et al. |
| 5,649,022 A | 7/1997 | Maeda et al. |
| 5,699,447 A | 12/1997 | Alumot et al. |
| 5,717,518 A | 2/1998 | Shafer et al. |
| 5,737,072 A | 4/1998 | Emery et al. |
| 5,768,443 A | 6/1998 | Michael et al. |
| 5,787,190 A | 7/1998 | Peng et al. |
| 5,822,055 A | 10/1998 | Tsai et al. |
| 5,825,483 A | 10/1998 | Michael et al. |
| 5,850,466 A | 12/1998 | Schott |
| 5,854,674 A | 12/1998 | Lin |
| 5,856,844 A | 1/1999 | Batterman et al. |
| 5,859,698 A | 1/1999 | Chau et al. |
| 5,859,923 A | 1/1999 | Petry, III et al. |
| 5,880,772 A | 3/1999 | Kalnajs et al. |
| 5,892,579 A | 4/1999 | Elyasaf et al. |
| 5,912,964 A | 6/1999 | Stelman |
| 5,913,105 A | 6/1999 | McIntyre et al. |
| 5,917,588 A | 6/1999 | Addiego |
| 5,923,430 A | 7/1999 | Worster et al. |
| 5,949,901 A | 9/1999 | Nichani et al. |
| 5,956,174 A | 9/1999 | Shafer et al. |
| 5,973,776 A | 10/1999 | Matsushita |
| 5,978,061 A | 11/1999 | Miyazaki et al. |
| 5,982,921 A | 11/1999 | Alumot et al. |
| 6,078,386 A | 6/2000 | Tsai et al. |
| 6,084,716 A | 7/2000 | Sanada et al. |
| 6,096,031 A | 8/2000 | Mitchell et al. |
| 6,122,397 A | 9/2000 | Lee et al. |
| 6,167,148 A | 12/2000 | Calitz et al. |
| 6,178,257 B1 | 1/2001 | Alumot et al. |
| 6,192,289 B1 | 2/2001 | Geffen et al. |
| 6,259,827 B1 | 7/2001 | Nichani |
| 6,317,512 B1 | 11/2001 | Maeda et al. |
| 6,324,298 B1 | 11/2001 | O'Dell et al. |
| 6,366,690 B1 | 4/2002 | Smilansky et al. |

(56) References Cited

U.S. PATENT DOCUMENTS

| | | | |
|---|---|---|---|
| 6,448,549 | B1 | 9/2002 | Safaee-Rad |
| 6,522,777 | B1 | 2/2003 | Paulsen et al. |
| 6,826,298 | B1 | 11/2004 | O'Dell et al. |
| 6,934,019 | B2 | 8/2005 | Geffen et al. |
| 7,060,115 | B2 | 6/2006 | Hashiguchi et al. |
| 7,729,528 | B2 | 6/2010 | O'Dell et al. |
| 9,337,071 | B2 * | 5/2016 | O'Dell ............... G01N 21/9501 |
| 2010/0239157 | A1 | 9/2010 | O'Dell et al. |
| 2012/0087569 | A1 | 4/2012 | O'Dell et al. |

FOREIGN PATENT DOCUMENTS

| | | |
|---|---|---|
| JP | 53024783 | 3/1978 |
| JP | 62220839 | 9/1987 |
| JP | 63058138 | 3/1988 |
| JP | 63083605 | 4/1988 |
| JP | 1169305 | 7/1989 |
| JP | 03018708 | 1/1991 |
| JP | 4104043 | 4/1992 |
| JP | 4348050 | 12/1992 |
| JP | 5006928 | 1/1993 |
| JP | 5218160 | 8/1993 |
| JP | 5281151 | 10/1993 |
| JP | 06036016 | 2/1994 |
| JP | 06069059 | 3/1994 |
| JP | 6165444 | 6/1994 |
| JP | 6258239 | 9/1994 |
| JP | 07058175 | 3/1995 |
| JP | 07099547 | 4/1995 |
| JP | 7190739 | 7/1995 |
| JP | 08094534 | 4/1996 |
| JP | 8272078 | 10/1996 |
| JP | 09-203621 | 5/1997 |
| JP | 09-252035 | 9/1997 |
| JP | 093055764 | 11/1997 |
| JP | 10074812 | 3/1998 |
| JP | 2006084444 | 3/2006 |
| JP | 2006084445 | 3/2006 |
| JP | 2007327815 | 12/2007 |
| JP | 2010151666 | 7/2010 |
| WO | 9107683 | 5/1991 |
| WO | 9111093 | 7/1991 |
| WO | 0000448 | 1/2000 |

OTHER PUBLICATIONS

*August Technology Corporation* v. *Camtek Ltd.*, Transcript of Thomas Verburgt Deposition dated Jan. 9, 2007; 20 pages.
*August Technology Corporation* v. *Camtek Ltd.*, Plaintiff's Responses to Camtek Ltd.'s Second Set of Requests for Admission to Plaintiff's No. 48-55) filed Jan. 19, 2007; 7 pages.
*August Technology Corporation* v. *Camtek Ltd.*, Plaintiff's Responses to Defendant's Third Request for the Production of Documents and Things (Nos. 94-103) filed Jan. 19, 2007; 8 pages.
*August Technology Corporation* v. *Camtek Ltd.*, Plaintiff's Response to Defendant's Interrogatory No. 18 filed Jan. 19, 2007; 3 pages.
*August Technology Corporation* v. *Camtek Ltd.*, Transcript of Jeffrey O'Dell Deposition dated Jan. 24, 2007; 84 pages.
*August Technology Corporation* v. *Camtek Ltd.*, Transcript of Mayson Brooks Deposition dated Feb. 5, 2007; 75 pages.
*August Technology Corporation* v. *Camtek Ltd.*, Transcript of Jeffrey O'Dell Deposition dated Feb. 6, 2007; 105 pages.
*August Technology Corporation* v. *Camtek Ltd.*, Camtek's Motion to Compel filed May 25, 2007 2 pages.
*August Technology Corporation* v. *Camtek Ltd.*, Memorandum of Law in Support of Plaintiff's Motion to Compel Production of Falcon Source Code Revision History filed May 25, 2007; 5 pages.
*August Technology Corporation* v. *Camtek Ltd.*, Expert Report of David L. Adler, PhD dated Jun. 20, 2007; 554 pages.
*August Technology Corporation* v. *Camtek Ltd.*, Plaintiff's Amended Responses to Camtek Ltd.'s Second Set of Requests for Admission to Plaintiffs (Nos. 48-55) filed Aug. 2, 2007; 8 pages.

*August Technology Corporation* v. *Camtek Ltd.*, Expert Report of John Phillip Mellor, Ph.D dated Aug. 3, 2007; 180 pages.
*August Technology Corporation* v. *Camtek Ltd.*, Rebuttal to Expert Report of John Hillip Mellor, Ph.d, dated Aug. 3, 2007; 16 pages.
*August Technology Corporation* v. *Camtek Ltd.*, Declaration of Rachel Zimmerman in Support of Plaintiff's Opposition to Camtek's Motion to Compel filed Sep. 17, 2007; 3 pages.
*August Technology Corporation* v. *Camtek Ltd.*, Order filed Oct. 3, 2007; 7 pages.
*August Technology Corporation* v. *Camtek Ltd.*, Order filed Nov. 21, 2007; 2 pages.
*August Technology Corporation* v. *Camtek Ltd.*, Transcript of Paul Kempf Deposition dated Dec. 6, 2007; 25 pages.
*August Technology Corporation* v. *Camtek Ltd.*, Memorandum Opinion and Order filed Jan. 3, 2008; 29 pages.
*August Technology Corporation* v. *Camtek Ltd.*, Camtek Ltd.'s Memorandum of Law in Support of its Motion for Summary Judgment of Invalidity of U.S. Pat. No. 6,826,298 filed Feb. 8, 2008; 12 pages.
*August Technology Corporation* v. *Camtek Ltd.*, Camtek's Memo in Support of Motion for Summary Judgment and Declaration of Autuoro with Exhibits A-C dated Feb. 8, 2008; 34 pages.
*August Technology Corporation* v. *Camtek Ltd.*, Camtek's Motion for Summary Judgment of Invalidity of U.S. Pat. No. 5,826,298 filed Feb. 8, 2008; 2 pages.
*August Technology Corporation* v. *Camtek Ltd.*, Plaintiff's Memorandum in Opposition to Defendant's Motion for Summary Judgment filed Mar. 14, 2008; 13 pages.
*August Technology Corporation* v. *Camtek Ltd.*, Plaintiffs Memo in Opposition to Defendant's Motion for Summary Judgment and Declaration of Lee with Exhibits A-N dated Mar. 14, 2008; 76 pages.
*August Technology Corporation* v. *Camtek Ltd.*, Memorandum Opinion and Order dated Jul. 14, 2008; 11 pages.
*August Technology Corporation* v. *Camtek Ltd.*, Camtek's Proposed Findings of Fact and Conclusions of Law dated Oct. 8, 2008; 3 pages.
*August Technology Corporation* v. *Camtek Ltd.*, Plaintiffs Proposed Findings of Fact and Conclusions of Law dated Oct. 8, 2008; 16 pages.
*August Technology Corporation* v. *Camtek Ltd.*, Plaintiff's Second Motion in Limine re Inequitable Conduct with Declaration of Lee and Exhibits dated Oct. 8, 2008; 106 pages.
*August Technology Corporation* v. *Camtek Ltd.*, Order dated Feb. 1, 2009; 2 pages.
*August Technology Corporation* v. *Camtek Ltd.*, Trial Transcript dated Feb. 2, 2009; pp. 1-501.
*August Technology Corporation* v. *Camtek Ltd.*, Trial Transcript dated Feb. 2, 2009; pp. 502-1001.
*August Technology Corporation* v. *Camtek Ltd.*, Trial Transcript dated Feb. 2, 2009; pp. 1002-1498.
*August Technology Corporation* v. *Camtek Ltd.*, Trial Transcript dated Feb. 2, 2009; pp. 1499-1997.
*August Technology Corporation* v. *Camtek Ltd.*, Trial Transcript dated Feb. 2, 2009; pp. 1998-2448.
*August Technology Corporation* v. *Camtek Ltd.*, Trial Transcript dated Feb. 2, 2009; pp. 2449-2865.
*August Technology Corporation* v. *Camtek Ltd.*, Verdict from *August* v. *Camtek* Trial dated Mar. 5, 2009; 9 pages.
*August Technology Corporation* v. *Camtek Ltd.*, Plaintiffs Memorandum of Law in Support of Motion for Entry of Judgment, Permanent Injunctions, Prejudgment Interest, and Accounting for Supplemental Damages, Declaration of Hughey (with Exhibits 1, 6-18), Declaration of Brooks, and Declaration of McCloskey dated Mar. 27, 2009; 296 pages.
*August Technology Corporation* v. *Camtek Ltd.*, Camtek's Memorandum of Law in Support of Motion to Defer Briefing and Decision on Plaintiff's Motion with Declaration of Autuoro and Exhibits 1-4 dated Apr. 14, 2009; 78 pages.
*August Technology Corporation* v. *Camtek Ltd.*, Plaintiff's Combined Memorandum in Opposition to Motion to Defer and Motion

(56) References Cited

OTHER PUBLICATIONS to Dismiss Defendant's Inequitable Conduct Defense and Counterclaim and Declaration of Lee with Exhibits 1-6 dated Apr. 17, 2009; 45 pages.
*August Technology Corporation* v. *Camtek Ltd.*, Camtek's Memorandum in Opposition to Plaintiff's Motion for Entry of Judgment and to Dismiss Inequitable Conduct, Declaration of Autuoro with Exhibits 1, 3-24, and Declaration of Troxel with Exhibits A-C; dated Jun. 19, 2009; 402 pages.
*August Technology Corporation* v. *Camtek Ltd.*, Plaintiff's Reply in Support of Motion for Entry of Judgment and to Dismiss Inequitable Conduct dated Jul. 10, 2009; 17 pages.
*August Technology Corporation* v. *Camtek Ltd.*, Order on Plaintiff's Motion to Dismiss Inequitable Conduct Defense dated Aug. 25, 2009; 16 pages.
*August Technology Corporation* v. *Camtek Ltd.*, Order on Final Judgement dated Aug. 28, 2009; 9 pages.
*August Technology Corporation* v. *Camtek Ltd.*, Camtek's Memorandum in Support of its Motion for Judgment as a Matter of Law of no Literal Infringement of U.S. Pat. No. 6,826,298 or, in the Alternative, for a New Trial on Literal Infringement dated Sep. 14, 2009, 29 pages.
*August Technology Corporation* v. *Camtek Ltd.*, Camtek's Memorandum in Support of its Motion for Judgment as a Matter of Law That the Asserted Claims of the 298 Patent are Invalid for Obviousness, or, in the Alternative, for a New Trial dated Sep. 14, 2009, 23 pages.
*August Technology Corporation* v. *Camtek Ltd.*, Plaintiff's Opposition to Motion for Judgment as a Matter of Law as a Matter of Law That the 298 Patent Claims are invalid and Alternative Motion for a New trial dated Oct. 19, 2009; 29 pages.
*August Technology Corporation* v. *Camtek Ltd.*, Plaintiff's Opposition to Motion for Judgment as a Matter of Law of No Literal Infringement and Camtek's Alternative Motion for a New Trial on Literal Infringement dated Oct. 19, 2009; 35 pages.
*August Technology Corporation* v. *Camtek Ltd.*, Camtek's Reply in Support of its Motion for Judgment as a Matter of Law of No Literal Infringement, dated Nov. 11, 2009, 20 pages.
*August Technology Corporation* v. *Camtek Ltd.*, Camtek's Reply in Support of its Motion for Judgment as a Matter of Law that the Asserted Claims of the '6,298 Patent are Invalid for Obviousness, Nov. 11, 2009, 19 pages.
*August Technology Corporation* v. *Camtek Ltd.*, Civil Action No. 10-2202, Complaint dated Jun. 1, 2010; 8 pages.
Right of Appeal Notice in Control No. 95/001,874, Feb. 1, 2013, 17 pages.
*Rudolph Technologies, Inc.* v. *Camtek, Ltd.*, Appeal No. 2015-1418, United States Court of Appeals for the Federal Circuit, Corrected Brief of Appellant Rudolph Technologies, Inc., Jul. 13, 2015, 112 pages.
*Rudolph Technologies, Inc.* v. *Camtek, Ltd.*, Appeal No. 2015-1418, United States Court of Appeals for the Federal Circuit, Motion for Judicial Notice and Exhibit 1, Aug. 26, 2015, 19 pages.
*Rudolph Technologies, Inc.* v. *Camtek, Ltd.*, Appeal No. 2015-1418, United States Court of Appeals for the Federal Circuit, Response Brief of Appellee Camtek Ltd., Aug. 27, 2015, 52 pages.
*Rudolph Technologies, Inc.* v. *Camtek, Ltd.*, Appeal No. 2015-1418, United States Court of Appeals for the Federal Circuit, Appellant's Response to Motion for Judicial Notice, Aug. 27, 2015, 5 pages.
*Rudolph Technologies, Inc.* v. *Camtek, Ltd.*, Appeal No. 2015-1418, United States Court of Appeals for the Federal Circuit, Appellee's Reply in Support of Motion for Judicial Notice, Aug. 31, 2015, 4 pages.
*Rudolph Technologies, Inc.* v. *Camtek, Ltd.*, Appeal No. 2015-1418, United States Court of Appeals for the Federal Circuit, Order, Sep. 16, 2015, 2 pages.
*Rudolph Technologies, Inc.* v. *Camtek, Ltd.*, Appeal No. 2015-1418, United States Court of Appeals for the Federal Circuit, Reply Brief of Appellant Rudolph Technologies, Inc., Sep. 21, 2015, 35 pages.

Solid State Technology, "Solid State, Automated Optical Inspection and Test of Active Matrix Liquid Crystal Arrays," 6 pages (Apr. 1995).
Solid State Technology, "Solid State," Worldwide Semiconductor Production, A PennWell Publication, 6 pages (Jun. 1993).
Third Party Requester Respondent Brief in Control No. 95/001,874, May 28, 2013, 20 pages.
Third Party Requester's Rebuttal Brief in Control No. 95/001,874, Aug. 30, 2013, 8 pages.
United States Court of Appeals for the Federal Circuit Decision in 0:05-cv-1396-MJD-AJB, Decided Aug. 22, 2011, 22 pages.
Yasuyuki Wakisaka et al., "Special Introduction of New Process and New Materials and Semiconductor Manufacturing Device Wafer Pattern Inspection Device 'Inspectra'" pp. 107-110 (Mar. 1996).
*August Technology Corporation* v. *Camtek Ltd.*, Memorandum of Law & Order dated Jul. 27, 2010; 20 pages.
*August Technology Corporation* v. *Camtek Ltd.*, Civil Action No. 10-2202, Amended Complaint dated Dec. 7, 2010; 46 pages.
*August Technology Corporation* v. *Camtek Ltd.*, Plaintiffs Memorandum in Support of Emergency Motion for Enforcement of the Permanent Injunction and for Attorneys' Fees dated Dec. 3, 2010; 16 pages.
*August Technology Corporation* v. *Camtek Ltd.*, Civil Action No. 10-2202, Order dismissing the case dated May 3, 2011; 1 page.
*August Technology Corporation* v. *Camtek Ltd.*, Civil Action No. 10-2202, Stipulated Dismissal Without Prejudice dated Apr. 15, 2011; 2 pages.
*August Technology Corporation* v. *Camtek Ltd.*, Civil Action No. 11-3707, Complaint dated Dec. 27, 2011; 5 pages.
*August Technology Corporation* v. *Camtek Ltd.*, Civil Action No. 11-3707, Stipulation to Stay Proceedings Pending completion of the Reexamination of the '528 Patent dated Apr. 18, 2012; 3 pages.
*August Technology Corporation* v. *Camtek Ltd.*, Civil Action No. 11-3707, Order Denying Stipulation to Stay and Granting Motion for Extension of Time dated May 1, 2012; 2 pages.
*August Technology Corporation* v. *Camtek Ltd.*, Civil Action No. 11-3707, Stipulation to stay proceedings pending completion of the Reexamination of the '528 patent dated May 2, 2012; 3 pages.
*August Technology Corporation* v. *Camtek Ltd.*, Civil Action No. 11-3707, Order granting in part the stipulation to stay proceedings pending completion of the reexamination of the '528 patent dated May 3, 2012; 2 pages.
*August Technology Corporation* v. *Camtek Ltd.*, Defendant's Opposition to Plaintiffs' "Emergency Motion for Enforcement of the Permanent Injunction" dated Dec. 17, 2010; 37 pages.
*August Technology Corporation* v. *Camtek Ltd.*, Memorandum of Law & Order dated Feb. 23, 2011; 6 pages.
August Technology, "NSX-80 Automated Wafer & Die Defect Inspection System (2nd Optical)," 21 pages (Mar. 1997).
August Technology, "NSX-80 Market Specifications and Top Potential Customers," 3 pages (Sep. 5, 1996).
B.B. Weiner et al., "Improvements in Accuracy and Speed Using the Time-of-Transition Method and Dynamic Image Analysis for Particle Sizing," 17 pages (1998).
Camtek Ltd.'s Prior Art Statement, U.S. District Court, District of Minnesota, Case No. 05-CV 1396 (MJD/AJB), 48 pages (Jul. 7, 2006).
Camtek's Motion for Judgment as a Matter of Law (JMOL); dated Jun. 22, 2009; 35 pages.
Camtek's Reply in Support of Motion for JMOL; dated Aug. 8, 2009; 15 pages.
Civil Docket for 0:10-cv-02202-MJD-FLN, filed on Jun. 1, 2010, 3 pages.
Complaint filed in the United States District Court for the District of Minnesota on Jul. 13, 2005, Civil Action No. 0:05-cv-01396.
Decision Dismissing Petitions under 37 C.F.R. 1.78(a)(3) and (a)(6) in U.S. Appl. No. 10/915,666 mailed on May 22, 2012.
Decision on Appeal in Control No. 95/001,874, Dec. 15, 2014, 23 pages.
Dralla, John and Hoff, John, "Automatic classification of defects in semiconductor devices," SPIE vol. 1261 Integrated circuit Metrology, Inspection, and Process Control IV, pp. 173-182 (1990).

(56) References Cited

OTHER PUBLICATIONS

Dralla, John, "Wafer inspection—past, present and future," Electronics Manufacture & Test, pp. 21-24 (May 1990).
IECON'91, 1991 International Conference on Industrial Electronics, Control and Instrumentation, "Computer Based Wafer Inspection System," 9 pages (Oct. 28-Nov. 1, 1991).
Inspection, Metrology and Data Analysis Solutions for Wafer Manufacturing and Final Processing, "August Technology Introduces Automated 2nd Optical Wafer & Die Inspection System," 1 page, San Jose, CA (Jul. 16, 1997).
Inter Partes Reexamination Examiner's Answer in Control No. 95/001,874, Jul. 31, 2013, 3 pages.
Japanese Office Action for Patent Application No. 2000-560537 mailed Apr. 21, 2009, 8 pages.
Japanese Office Action for Patent Application No. 2000-560537 mailed Nov. 12, 2009, 9 pages.
Japanese Office Action for Patent Application No. 2009-218183 mailed Aug. 3, 2010, 19 pages.
Japanese Office Action for Patent Application No. 2009-218183 mailed May 9, 2011, 8 pages.
Japanese Office Action for Patent Application No. 2009-218183 mailed Dec. 15, 2011, 11 pages.
Japanese Office Action for Japanese Patent Application No. 2011-022049 mailed Jun. 19, 2012, 13 pages.
Markman Hearing for 0:05-cv-1396-MJD-AJB, filed on Jan. 3, 2008, 29 pages.
Montellese, Steven, "Inspection: Making the Right Choice in Machine Vision Systems", Photonics Spectra, Sep. 1995, pp. 107-112.
Non-Final Office Action mailed Dec. 27, 2012 for U.S. Appl. No. 13/273,645, 22 pages.
Novini, Amir R., "Fundamentals of Strobe Lighting for Machine Vision", Society of Manufacturing Engineers: Technical Paper, 1991: MS91-399, 14 pages.
Office Action for Japanese Patent Appln. No. 2009-218183 mailed May 9, 2011, 8 pages.
Office Action for U.S. Appl. No. 13/273,645 mailed Jun. 26, 2013, 11 pages.
Office Action mailed Mar. 26, 2012, corresponding to Control No. 95/001,874 and U.S. Pat. No. 7,729,528, 46 pages.
Patent Owner's Brief on Appeal in Control No. 95/001,874, Apr. 30, 2013, 45 pages.
Petition to Claim Benefit under 35 U.S.C. 120, 1212, or 365(c) of a prior Copending Nonprovisional Application (35 C.F.R. 1.78(a)(3)) in U.S. Appl. No. 10/915,666, filed on Apr. 16, 2012.
Photonics Systems Group Automation Technology Division, SIMTech Technical Report (AT/01/038/PS) "Development of Automated Wafer Bump Inspection Technology," 7 pages (2001).
Plaintiffs Opposition to Motion for JMOL; dated Jul. 14, 2009; 26 pages.
Pleading Inventory for Case No. 05-CV-1396 as of Aug. 18, 2006, Pleading Index No. 1 through Pleading Index No. 13 listing items 1-241.
Record of Oral Hearing in Control No. 95/001,874, Feb. 6, 2015, 64 pages.
Request for Inter Parte Reexamination filed Jan. 19, 2012 corresponding to U.S. Pat. No. 7,729,528, pp. 1-165.
Request for Inter Parte Reexamination filed Jan. 19, 2012 corresponding to U.S. Pat. No. 7,729,528, pp. 166-331.
Request for Inter Parte Reexamination filed Jan. 19, 2012 corresponding to U.S. Pat. No. 7,729,528, pp. 332-496.
Request for Reconsideration of Petition to Claim Benefit under 35 U.S.C. 120, 121, or 365(c) of a prior Copending Nonprovisional Application (35 C.F.R. 1.78(a)(3)) in U.S. Appl. No. 10/915,666, filed on Jun. 26, 2012.
*August Technology Corporation v. Camtek Ltd.*, Plantiff's Complaint, filed Jul. 14, 2005; 5 pages.
*August Technology Corporation v. Camtek Ltd.*, Exhibit A to Complaint, filed Jul. 14, 2005; 31 pages.
*August Technology Corporation v.Camtek Ltd.*, Camtek Ltd.'s Responses and Objections to August Technology Corp.'s First Set of Requests for Production of Documents and Things, filed Oct. 28, 2005; 13 pages.
*August Technology Corporation v. Camtek Ltd.*, Defendant Camtek Ltd.'s Responses and Objections to August Technology Corp.'s First Set of Interrogatories, filed Oct. 28, 2005; 14 pages.
*August Technology Corporation v. Camtek Ltd.*, Memorandum & Order, filed Dec. 2, 2005; 11 pages.
*August Technology Corporation v. Camtek Ltd.*, Defendant's Responses to Plaintiff's First Set of Interrogatories, filed Dec. 19, 2005; 9 pages.
*August Technology Corporation v. Camtek Ltd.*, Defendant's Responses to Plaintiffs First Set of Requests for the Production of Documents and Things, filed Dec. 19, 2005; 14 pages.
*August Technology Corporation v. Camtek Ltd.*, Answer and Counterclaim of Camtek Ltd. in Response to Complaint of August Technology Corporation, filed Dec. 22, 2005; 9 pages.
*August Technology Corporation v. Camtek Ltd.*, Plaintiff's Responses to Defendant's First Request for the Production of Documents and Things, filed Jan. 6, 2006; 20 pages.
*August Technology Corporation v. Camtek Ltd.*, Plaintiff's Responses to Defendant's First Set of Interrogatories, filed Jan. 6, 2006; 6 pages.
*August Technology Corporation v. Camtek Ltd.*, Plaintiff's Reply to Counterclaim filed Jan. 11, 2006; 3 pages.
*August Technology Corporation v. Camtek Ltd.*, Camtek Ltd.'s Responses and Objections to August Technology Corp.'s Second Set of Requests for Production (Nos. 15-33) filed Apr. 3, 2006, 16 pages.
*August Technology Corporation v. Camtek Ltd.*, Camtek's Opposition to August's Motion to Compel Discovery filed Apr. 6, 2006; 15 pages.
*August Technology Corporation v. Camtek Ltd.*, Amended Complaint and Jury Demand and Exhibit A filed Apr. 12, 2006; 37 pages.
*August Technology Corporation v. Camtek Ltd.*, Answer and Counterclaim of Camtek Ltd. in Response to Amended complaint of August Technology Corporation and Rudolph Technologies, Inc. filed May 1, 2006; 11 pages.
*August Technology Corporation v. Camtek Ltd.*, Plaintiff's Reply to Defendant's Counterclaim filed May 24, 2006; 4 pages.
*August Technology Corporation v. Camtek Ltd.*, Rudolph's Responses to Defendant's First Request to Rudolph Technologies for the Production of Documents and Things (Nos. 1-90) filed Jun. 14, 2006; 35 pages.
*August Technology Corporation v. Camtek Ltd.*, August's Responses to Defendant's Second Request to August Technologies for the Production of Documents and Things (Nos. 41-93) filed Jun. 14, 2006; 22 pages.
*August Technology Corporation v. Camtek Ltd.*, Defendant Camtek Ltd.'s Response and Objections to Plaintiff's Third Set of Requests for the Production of Documents and Things (Nos. 34-48) filed Jun. 26, 2006; 14 pages.
*August Technology Corporation v. Camtek Ltd.*, Defendant Camtek Ltd.'s Response and Objections to Plaintiff's First Set of Admissions (1-66) filed Jun. 30, 2006; 57 pages.
*August Technology Corporation v. Camtek Ltd.*, Plaintiff August Technology Corporation's Amended Response to Defendant's Interrogatory No. 1 filed Jul. 13, 2006; 4 pages.
*August Technology Corporation v. Camtek Ltd.*, Disputed Claim Terms and Phrases filed Aug. 4, 2006; 10 pages.
*August Technology Corporation v. Camtek Ltd.*, Joint Claim Construction Statement filed Aug. 4, 2006; 4 pages.
*August Technology Corporation v. Camtek Ltd.*, Plaintiff's Prior Art Statement filed Aug. 4, 2006; 24 pages.
*August Technology Corporation v. Camtek Ltd.*, Order filed Aug. 24, 2006; 6 pages.
*August Technology Corporation v. Camtek Ltd.*, Camtek Ltd.'s Opening Claim Construction Brief filed Sep. 12, 2006; 29 pages.
*August Technology Corporation v. Camtek Ltd.*, Plaintiff's Opening Claim Construction Brief filed Sep. 12, 2006; 34 pages.
*August Technology Corporation v. Camtek Ltd.*, Supplemental Joint Claim Construction Statement filed Sep. 12, 2006; 12 pages.

(56) References Cited

OTHER PUBLICATIONS

*August Technology Corporation v. Camtek Ltd.*, Transcript of Thomas Verburgt's Deposition dated Sep. 21, 2006; 46 pages.
*August Technology Corporation v. Camtek Ltd.*, Transcript of Jeffrey O'Dell's Deposition dated Sep. 22, 2006; 30 pages.
*August Technology Corporation v. Camtek Ltd.*, Camtek Ltd.'s Amended Responses to Plaintiff's Requests for Admission Nos. 35-37 filed Sep. 26, 2006; 7 pages.
*August Technology Corporation v. Camtek Ltd.*, Transcript of Cory Watkins Deposition dated Sep. 28, 2006; 76 pages.
*August Technology Corporation v. Camtek Ltd.*, Transcript of Mark Harless Deposition dated Sep. 29, 2006; 65 pages.
*August Technology Corporation v. Camtek Ltd.*, Plaintiff's Rebuttal Claim Construction Brief filed Oct. 6, 2006; 10 pages.
*August Technology Corporation v. Camtek Ltd.*, Plaintiff's Responses to Camtek Ltd.'s First Set of Interrogatories for Admission to Plaintiffs (Nos. 1-47) filed Nov. 17, 2006; 23 pages.
*August Technology Corporation v. Camtek Ltd.*, Amended Answer and Counterclaim of Camtek Ltd. in Response to Amended Complaint of August Technology Corporation and Rudolph Technologies, Inc. filed Nov. 17, 2006; 14 pages.
*August Technology Corporation v. Camtek Ltd.*, Plaintiff's Responses to Defendant's Interrogatories Nos. 7-17 filed Nov. 20, 2006; 9 pages.
*August Technology Corporation v. Camtek Ltd.*, Plaintiff's Answers to Defendant's Interrogatory No. 11 and Referenced Documents dated Nov. 20, 2006; 9 pages.
*August Technology Corporation v. Camtek Ltd.*, Defendant Camtek Ltd.'s Response and Objections to Plaintiff's Fifth Set of Requests for the Production of Documents and Things (Nos. 90-110) filed Dec. 4, 2006; 19 pages.
*August Technology Corporation v. Camtek Ltd.*, Defendant Camtek Ltd.'s Response and Objections to Plaintiff's Sixth Set of Requests for the Production of Documents and Things (Nos. 111-116) filed Dec. 11, 2006; 10 pages.
*August Technology Corporation v. Camtek Ltd.*, Second Amended Answer and Counterclaim of Camtek Ltd. in Response to Amended Complaint of August Technology Corporation and Rudolph Technologies, Inc., filed Dec. 15, 2006; 14 pages.
*August Technology Corporation v. Camtek Ltd.*, Camtek's Ltd.'s Amended Responses to Plaintiff's Requests for Admission (Nos. 3-5, 9-16, 22-28, 33-34, 38, 40-45, 51-54) filed Dec. 18, 2006; 42 pages.
*August Technology Corporation v. Camtek Ltd.*, Defendant Camtek Ltd.'s Response and Objections to Plaintiff's Second Set of Request for Admissions (67-114) filed Dec. 18, 2006; 16 pages.
*August Technology Corporation v. Camtek Ltd.*, Defendant Camtek Ltd.'s Response and Objections to Plaintiff's Third Set of Requests for Admission (115-161) filed Dec. 18, 2006; 23 pages.
*August Technology Corporation v. Camtek Ltd.*, Defendant Camtek Ltd.'s Response and Objections to Plaintiff's Fourth Set of Requests for Admissions (162-203) filed Dec. 18, 2006; 27 pages.
*August Technology Corporation v. Camtek Ltd.*, Plaintiff's Amended Responses to Camtek Ltd.'s First Set of Requests for Admission to Plaintiffs filed Dec. 18, 2006; 15 pages.
*August Technology Corporation v. Camtek Ltd.*, Transcript of John Vasuta Deposition dated Dec. 20, 2006; 74 pages.
*August Technology Corporation v. Camtek Ltd.*, Transcript of Stan Piekos Deposition dated Dec. 21, 2006; 63 pages.
*August Technology Corporation v. Camtek Ltd.*, Plaintiff's Reply to Camtek's Second Amended Answer and counterclaim filed Jan. 5, 2007; 4 pages.
*August Technology Corporation v. Camtek Ltd.*, Subpoena in a Civil Case dated Jan. 5, 2007; 13 pages.

* cited by examiner

AUTOMATED WAFER DEFECT INSPECTION SYSTEM AND A PROCESS OF PERFORMING SUCH INSPECTION

BACKGROUND

The present invention relates to defect inspection systems for the semiconductor industry. More particularly, the present invention relates to an automated defect inspection system for patterned wafers, whole wafers, sawn wafers such as on film frames, JEDEC trays, Auer boats, die in gel or waffle packs, multi-chip modules often referred to as MCMs, etc., that is specifically intended and designed for second optical wafer inspection for such defects as metalization defects (such as scratches, voids, corrosion, and bridging), diffusion defects, passivation layer defects, scribing defects, glassivation defects, chips and cracks from sawing, and bump or bond pad area defects such as gold or solder bump defects or similar interconnect defects. Specifically, the present invention is an automated defect inspection system for integrated circuits, LCD panels with photolithography circuitry embedded therein, etc., where the system is used as follows: the system is trained by viewing a plurality of known good die under an imaging head resulting in a good die model, an inspection recipe is inputted into the system to define inspection parameters, defect inspection occurs where die are loaded onto, aligned in and viewed by an imaging head for defects in comparison to the good die model, an optional review of the identified defects may occur, and the user may optionally receive or export a report thereon.

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors.

One process that has evolved over the past decade or so is the semiconductor inspection process. The merit in inspecting semiconductors throughout the manufacturing process is obvious in that bad wafers may be removed at the various steps rather than processed to completion only to find out a defect exists either by end inspection or by failure during use.

A typical example of the semiconductor manufacture process is summarized as follows. Bare whole wafers are manufactured. Thereafter, circuitry is created on the bare whole wafers. The whole wafer with circuitry is then sawn into smaller pieces known in the industry as die. Thereafter, the die are processed, as is well known in the art, typically as die in waffle and/or gel packs or on substrates.

Today, it is well known that various inspection processes occur during this semiconductor process. Bare wafer inspection may occur on bare whole wafers not long after initial creation from sand and/or after polishing of the wafer but always prior to the deposit of any layers that form the circuitry. Defects being inspected for during bare wafer inspection include surface particulates and surface imperfections or irregularities.

During the deposition of layers, that is the circuit building, on the whole wafer, one or more first optical inspections may occur. First ($1^{st}$) optical inspection is "in process" inspection of wafers during circuitry creation. This $1^{st}$ inspection may be after each layer is deposited, at certain less often intervals, or only once during or after all deposits. This $1^{st}$ optical inspection is usually a sub-micron level inspection in the range of 0.1 micron to <1 micron. This process is used to check for mask alignment or defects such as extra metal, missing metal, contaminants, etc. This $1^{st}$ inspection occurs during circuitry development on the wafer.

Once the whole wafers are at least fully deposited on, that is all of the circuitry is created thereon, a post $1^{st}$ (or 1.5) inspection occurs on the fully processed whole wafers. Generally, this is prior to the deposit of a passivation layer although it need not be. In addition, this post $1^{st}$ inspection is generally prior to electrical testing or probing of the whole wafers. This inspection is typically a 0.5 micron to 1 micron optical inspection.

After the whole wafers are fully processed, one or more $2^{nd}$ optical inspections are performed. Front end $2^{nd}$ optical inspections occur after the whole wafers are fully processed and, if probing is necessary, just before or right after this probing or electrical testing to determine the quality of the devices. Back end $2^{nd}$ optical inspections occur at various stages such as during the applying of bumps to the die or wafer, during or after sawing of the wafers into sawn wafers, during or after dicing of the wafers, during or after picking up and placing of the die onto other packages such as trays or waffle or gel packs, during or after placing of the wafers onto a substrate, etc. This $2^{nd}$ optical inspection is generally at a 1+ micron level and is generally looking for defects such as metalization defects (such as scratches, voids, corrosion, and bridging), diffusion defects, passivation layer defects, scribing defects, glassivation defects, chips and cracks from sawing, and probe or bond pad area defects.

After actual packaging, $3^{rd}$ optical inspections occur. This packaging involves at least one of the following: placing the die on a substrate, wire bonding the die, connecting the leads, attaching the balls to a flip chip, etc. At this point, the inspection involves inspecting the ball grid array, lead straightness, wire bonding, ink marking, and for any package defects such as chips, cracks and voids. This $3^{rd}$ level inspection is generally at a 5+ micron level.

The focus of the semiconductor inspection industry has been bare wafer and $1^{st}$ optical inspection. Numerous market leaders have developed, patented, and are manufacturing and marketing $1^{st}$ optical inspection systems to perform these inspections including ADE, KLA, Tencor, Inspex, Applied, Orbit and others.

Often this equipment is very expensive and large. At the $1^{st}$ inspection stage, this expense and machine size issue is not as significant as at later inspection stages because only a relatively few parties manufacture the silicon wafers and thus need to inspect bare wafers in comparison to the vast number of companies that buy bare or sawn wafers and further process them into finished chips. These often expensive and large inspection devices are not cost justifiable for smaller shops and as such, inspection equipment is needed that satisfies this need at the $2^{nd}$ and $3^{rd}$ stages as well as is more economical for the vast many smaller companies that finish process wafers.

To a lesser extent, some resources have been spent on $3^{rd}$ optical inspection and several companies including STI, View Engineering, RVSI, and ICOS have developed systems for this purpose and are marketing those systems.

However, none of these systems address the particular and unique constraints of 2nd optical and this area has been largely ignored. In actual application, $2^{nd}$ optical inspection has been marginally performed by manual inspection using humans and microscopic equipment. This manual process is inaccurate due to various factors including stress, eye fatigue and boredom of the operator as well as different perceptions by different operators as to the significance of a finding. In addition, smaller circuit geometry and higher throughput requirements are increasing the demands on semiconductor inspection at this $2^{nd}$ optical level, all of which further results in operator stress, eye fatigue, and sometimes lower quality.

In addition at the $2^{nd}$ optical inspection stage to the need for inspecting for metalization defects (such as scratches, voids, corrosion, and bridging), diffusion defects, passivation layer defects, scribing defects, glassivation defects, chips and cracks from sawing, etc., bumps have taken on additional importance of recent. This is due to the recent surge in the use of bump interface connects, or flip chips, rather than leads which has magnified the importance of $2^{nd}$ optical inspection and thus the need for equipment and systems over manual inspection.

SUMMARY

It is an objective of the present invention to provide an automated inspection system that replaces the current manual inspection process.

It is a further objective of the present invention to provide a new, state of the art $2^{nd}$ optical inspection system.

It is further an objective of the present invention to provide an automated defect inspection system of patterned wafers, whole wafers, sawn wafers, JEDEC trays, Auer boats, die in gel or waffle packs, MCMs, etc.

It is further an objective of the present invention to provide an automated defect inspection system that is specifically intended and designed for second optical wafer inspection although useful in other levels of optical inspection such as level 1.5.

It is further an objective of the present invention to provide an automated defect inspection system for inspecting for defects such as metalization defects (such as scratches, voids, corrosion, and bridging), diffusion defects, passivation layer defects, scribing defects, glassivation defects, chips and cracks from sawing, probe area defects, bump area defects and/or bond pad area defects.

It is further an objective of the present invention to provide an automated defect inspection system that eliminates or significantly reduces the need for manual microscopic inspecting of every die in every wafer.

It is further an objective of the present invention to provide an automated defect inspection system that views the ever-smaller circuit geometry in an accurate and rapid manner.

It is further an objective of the present invention to provide an automated defect inspection system that provides for higher throughput than manual inspections.

It is further an objective of the present invention to provide an automated defect inspection system that provides for improved inspection quality and consistency.

It is further an objective of the present invention to provide an automated defect inspection system that provides for improved process control.

It is further an objective of the present invention to provide an automated defect inspection system that has inspection recipes therein and can create, copy and edit such recipes to customize the system to the user's inspection requirements.

It is further an objective of the present invention to provide an automated defect inspection system that uses digital image analysis to perform semiconductor wafer inspection.

It is further an objective of the present invention to provide an automated defect inspection system that is trained by inspecting good die so that once trained the system detects variations from what it has learned.

It is further an objective of the present invention to provide an automated defect inspection system that is trainable.

It is further an objectives of the present invention to provide an automated defect inspection system that develops a model of a good die and uses this model to inspect unknown quality die.

It is further an objective of the present invention to provide an automated defect inspection system that includes a "good die" training step and a defect inspection step using the good die model.

It is further an objective of the present invention to provide an automated defect inspection system that includes a "good die" training step, an inspection recipe creation step and a defect inspection step.

It is further an objective of the present invention to provide an automated defect inspection system that includes a "good die" training step, an inspection recipe creation step, a defect inspection step, a defect review step, and a report issuing or exporting step.

It is further an objective of the present invention to provide an automated defect inspection system that provides for multi-dimensional alignment of each wafer, substrate or other device having die thereon to be inspected such that every die is uniformly positioned.

It is further an objective of the present invention to provide an automated defect inspection system that provides for x, y and theta (θ) alignment of each wafer, substrate or other device having die thereon to be inspected such that every die is uniformly positioned.

It is further an objective of the present invention to provide an automated defect inspection system that provides for course alignment, fine alignment, and/or focusing of each wafer.

It is further an objective of the present invention to provide an automated defect inspection system that provides "good die" modeling by viewing multiple good dies and developing a model therefrom.

It is further an objective of the present invention to provide an automated defect inspection system that provides for defect inspection using an imaging head or camera to view static and properly aligned die.

It is further an objective of the present invention to provide an automated defect inspection system that provides for defect inspection using an imaging head or camera to view dynamic or moving yet properly aligned die.

It is further an objective of the present invention to provide an automated defect inspection system that provides for defect inspection using an imaging head or camera to view dynamic or moving yet properly aligned die where a strobe illumination is used to capture still views of the dynamically moving die.

It is further an objective of the present invention to provide an automated defect inspection system that provides for review of the system detected defects whereby the user need not look at all die or all parts of die and instead only views the marked or noted defects.

It is further an objective of the present invention to provide an automated defect inspection system that provides means for accounting for drifting or non-regularity of die positioning or spacing.

It is further an objective of the present invention to provide an automated defect inspection system that provides means to inspect die on a stretched film frame where the dies are irregularly spaced, rotated, drifted, etc.

It is further an objective of the present invention to provide an automated defect inspection system that provides a method to measure the size, position, shape, geometry, and other characteristics of solder bumps, gold bumps, bond pads or the like.

It is further an objective of the present invention to provide an automated defect inspection system that provides a method to inspect the quality of gold bumps, solder bumps, interconnects or the like, or the probe marks on bond pads.

It is further an objective of the present invention to provide an automated defect inspection system that provides a method to detect defects on bond pads, bumps or interconnects.

Still other advantages and benefits of the invention will become apparent to those skilled in the art upon a reading and understanding of the following summary, and detailed description.

Accordingly, the present invention satisfies these and other objectives as it, relates to automated inspection equipment, systems and processes. Specifically, the present invention is an automated method of inspecting a semiconductor wafer in any form, size and shape including whole patterned wafers, sawn wafers, broken wafers, partial wafers, and wafers of any kind on film frames, dies, die in gel paks, die in waffle paks, multi-chip modules often called MCMs, JEDEC trays, Auer boats, and other wafer and die package configurations for defects, the method or apparatus comprising training a model as to parameters of a good wafer via optical viewing of multiple known good wafers, illuminating unknown quality wafers using at least one of a brightfield illuminator positioned approximately above, a darkfield illuminator positioned approximately above, and a darkfield laser positioned approximately about the periphery of a wafer test plate on which the wafer is inspected, all of which are for providing illumination to the unknown quality wafers during inspection and at least one of which strobes during inspection, and inspecting unknown quality wafers using the model.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DETAILED DESCRIPTION

Figure 1:
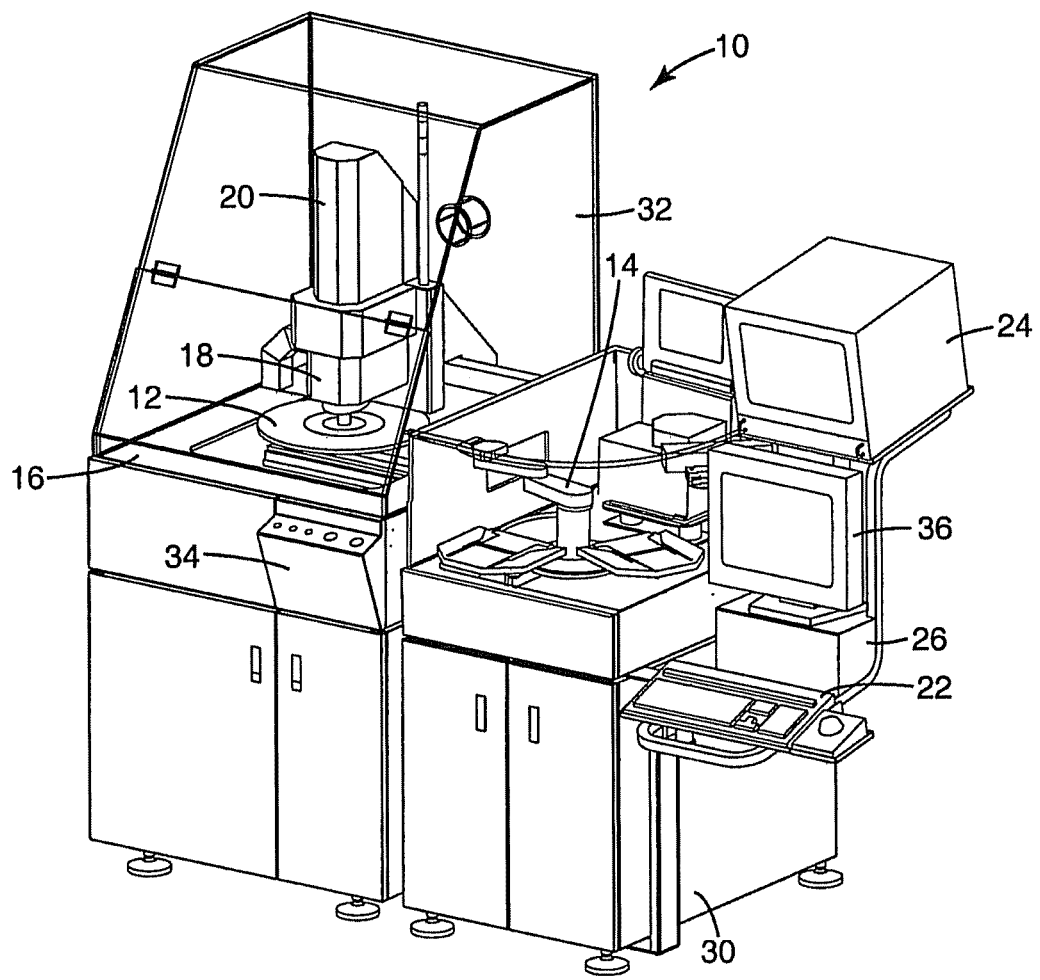
FIG. 1 is a perspective view of one embodiment of the system.
Figure 8:
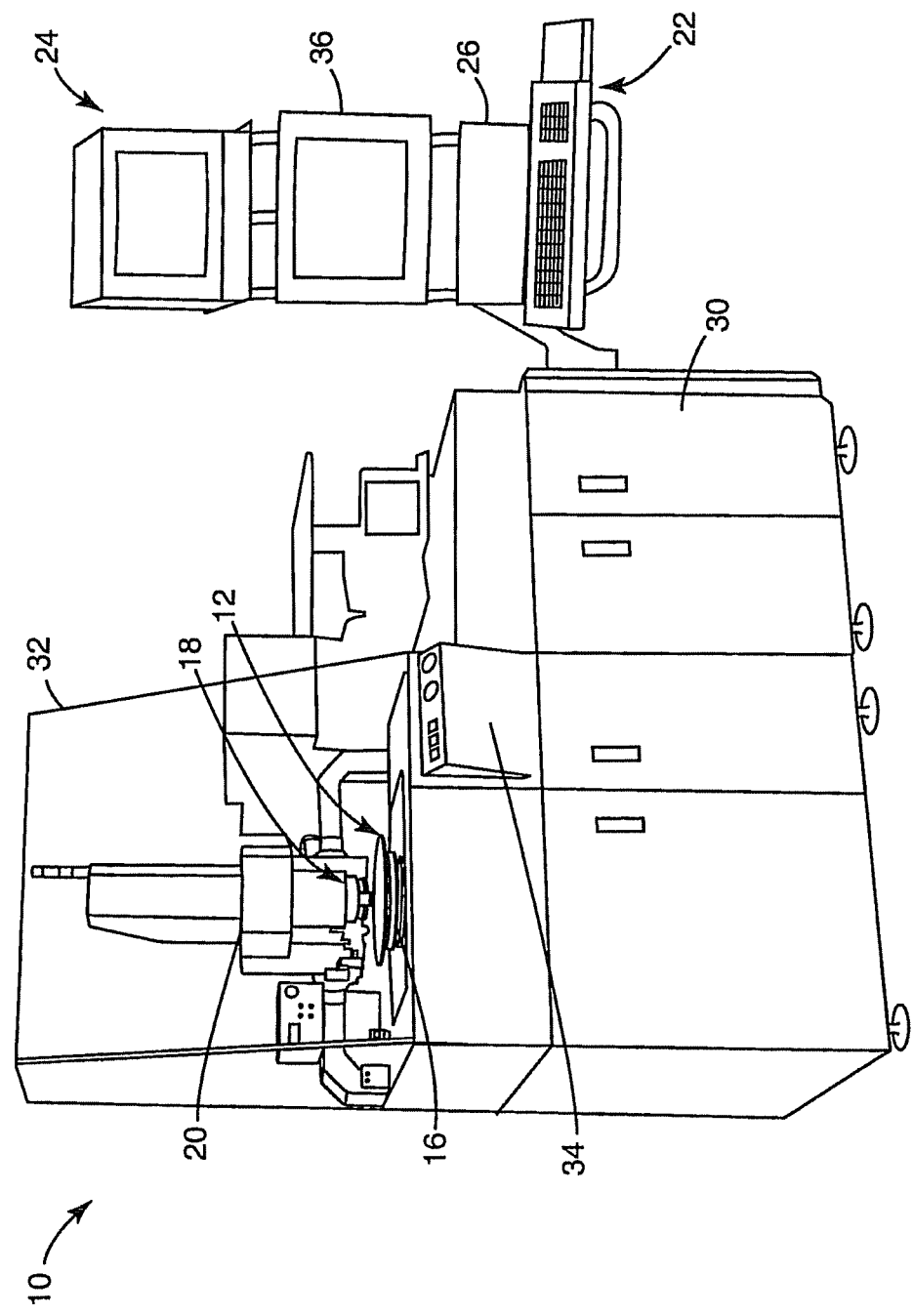
FIG. 8 is an overall perspective view of a similar system to that shown in FIG. 1 taken at a different angle.
Figure 9:
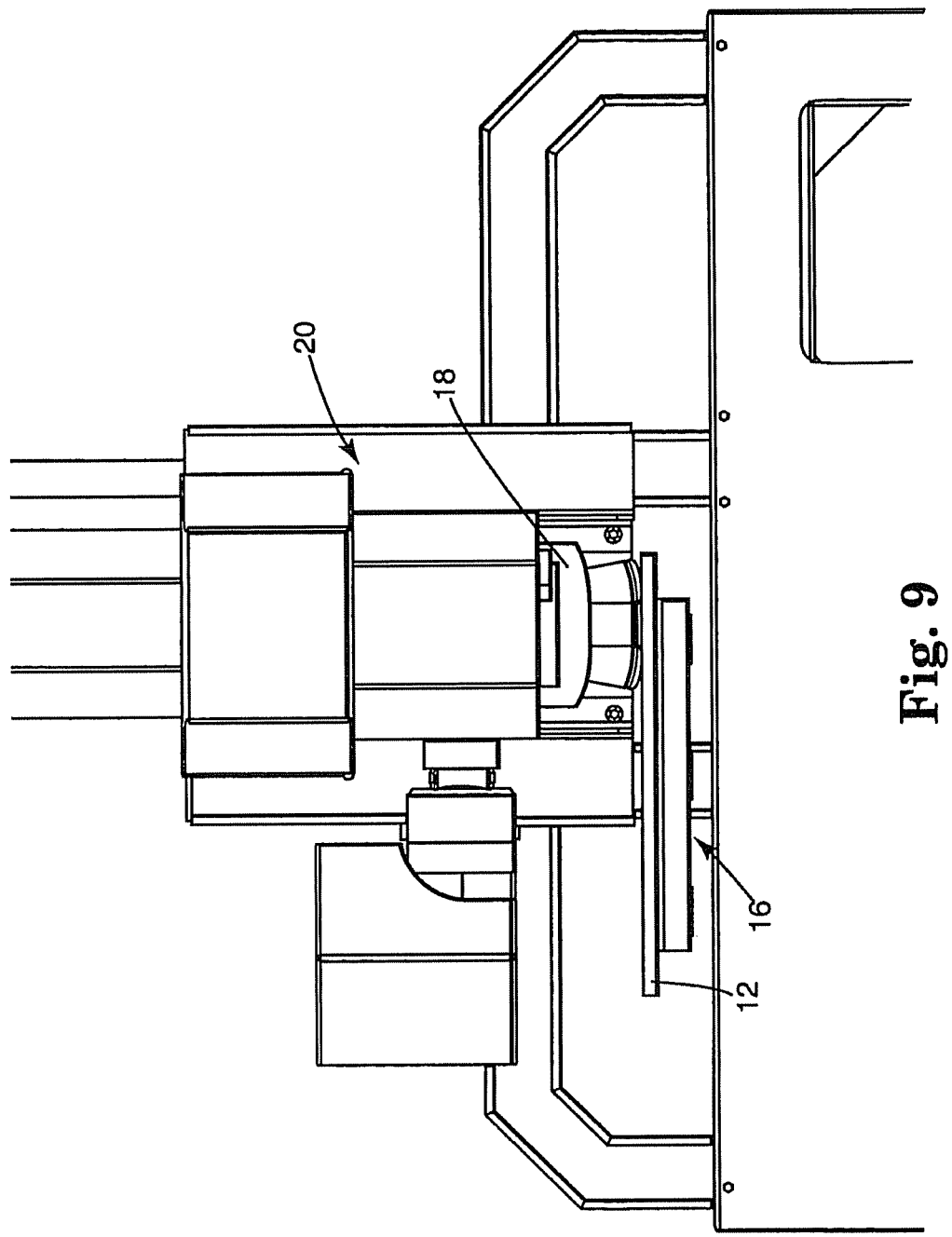
FIG. 9 is a front view of the wafer top plate and optics.
Figure 10:
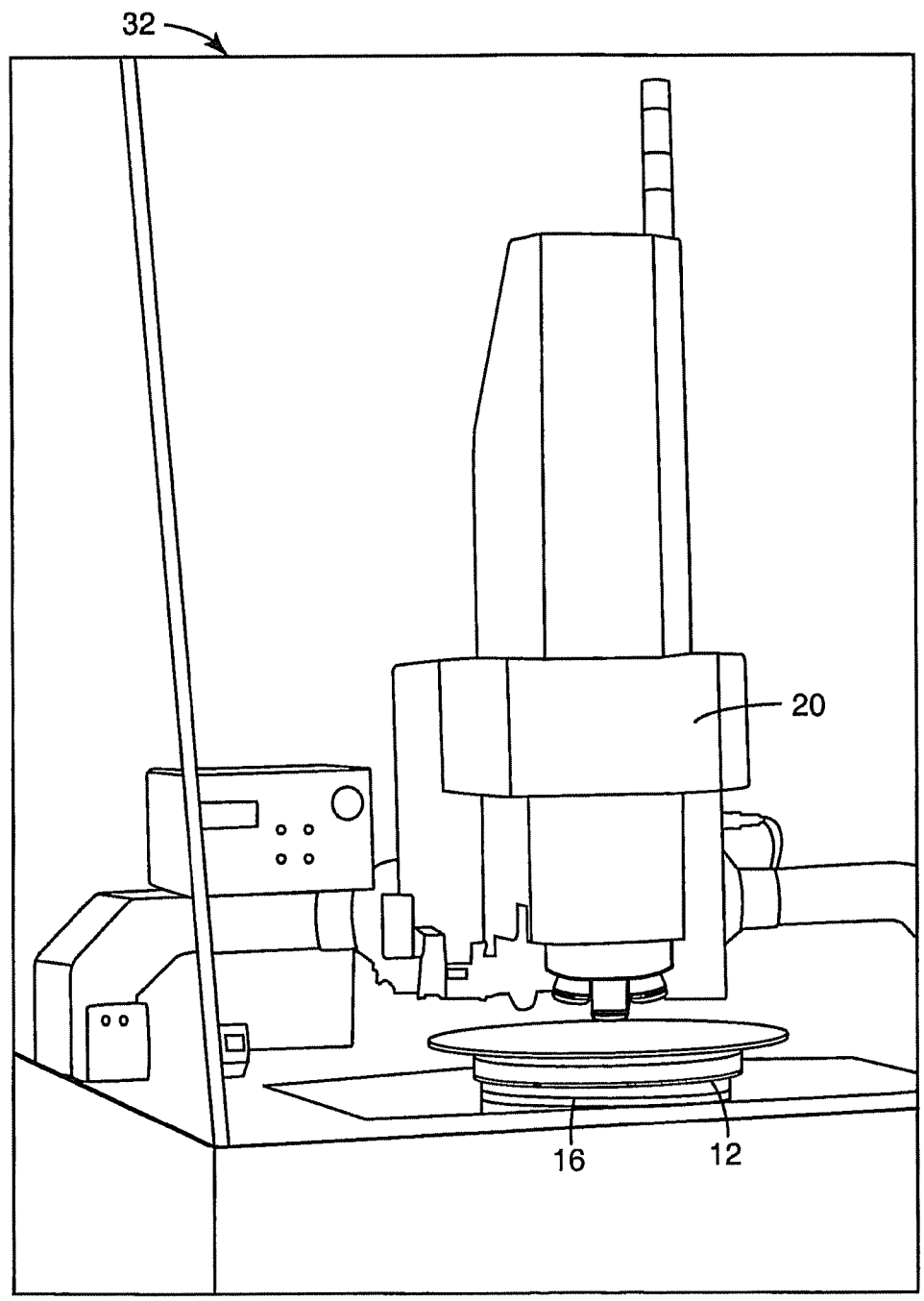
FIG. 10 is a left front perspective view of a portion of the inspection station including the wafer top plate and optics.
Figure 11:
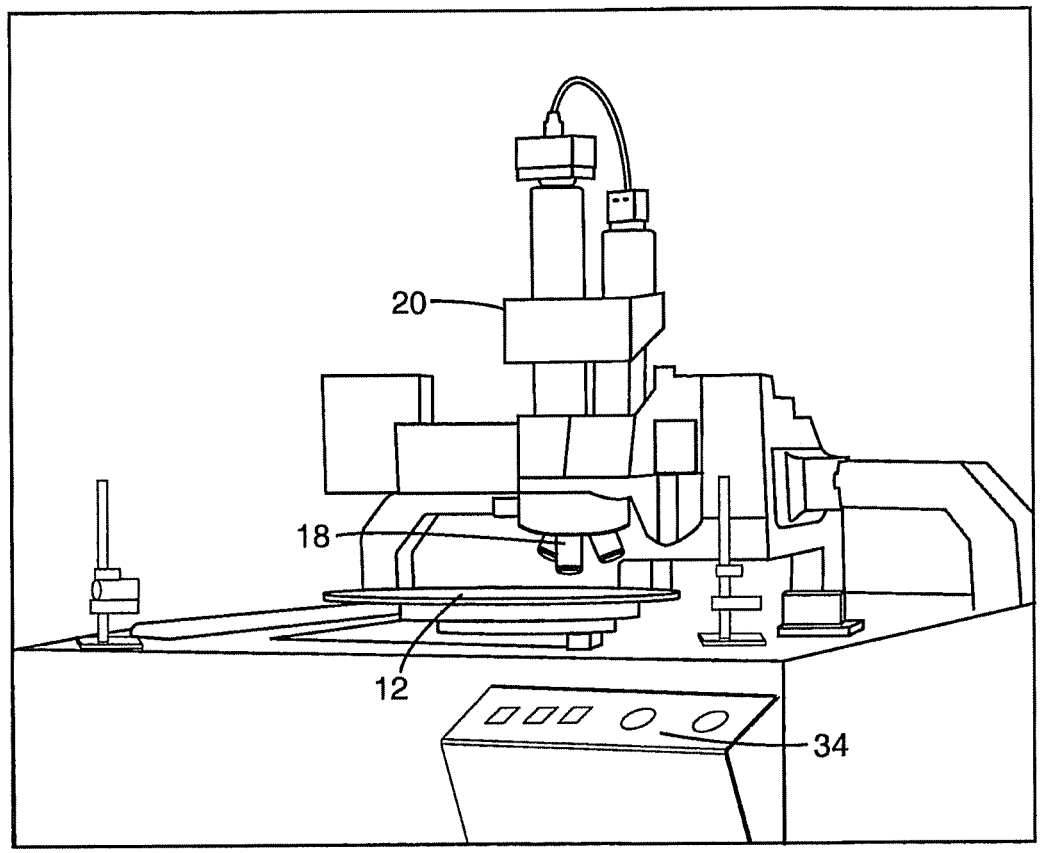
FIG. 11 is a right front perspective view of the top portion of the inspection station.
Figure 12:
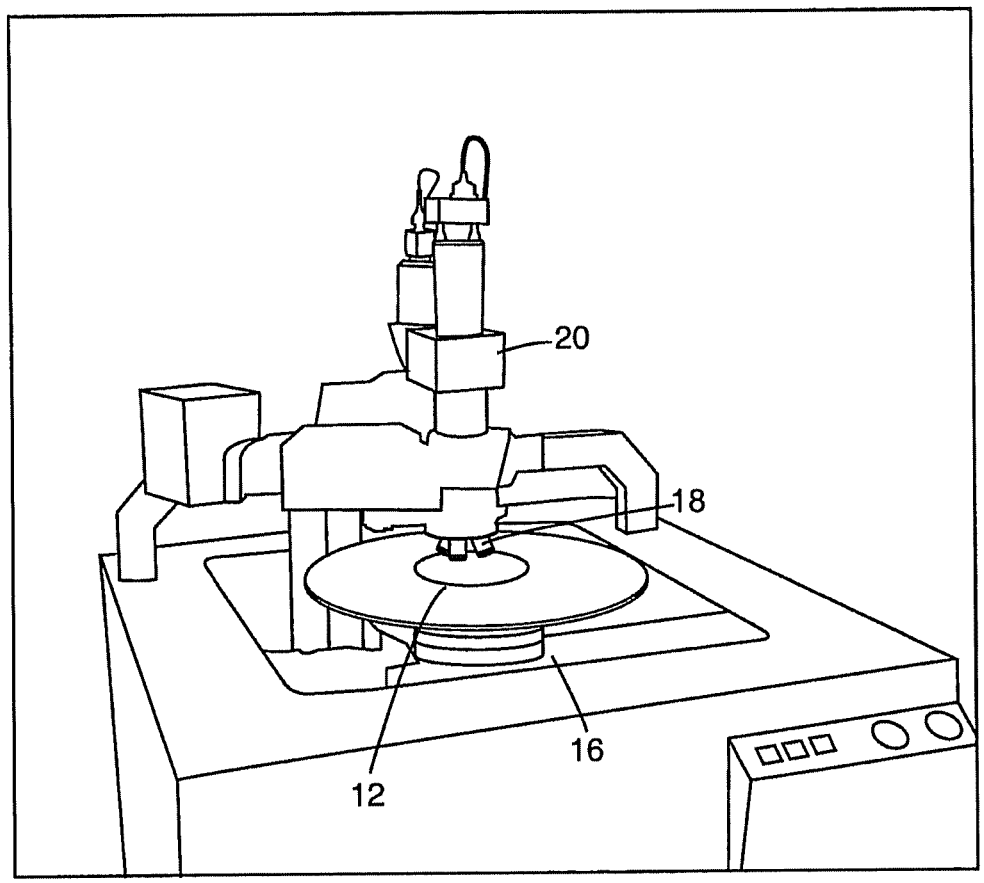
FIG. 12 is a side perspective view of the top portion of the inspection station as shown in FIG. 11.
Figure 13:
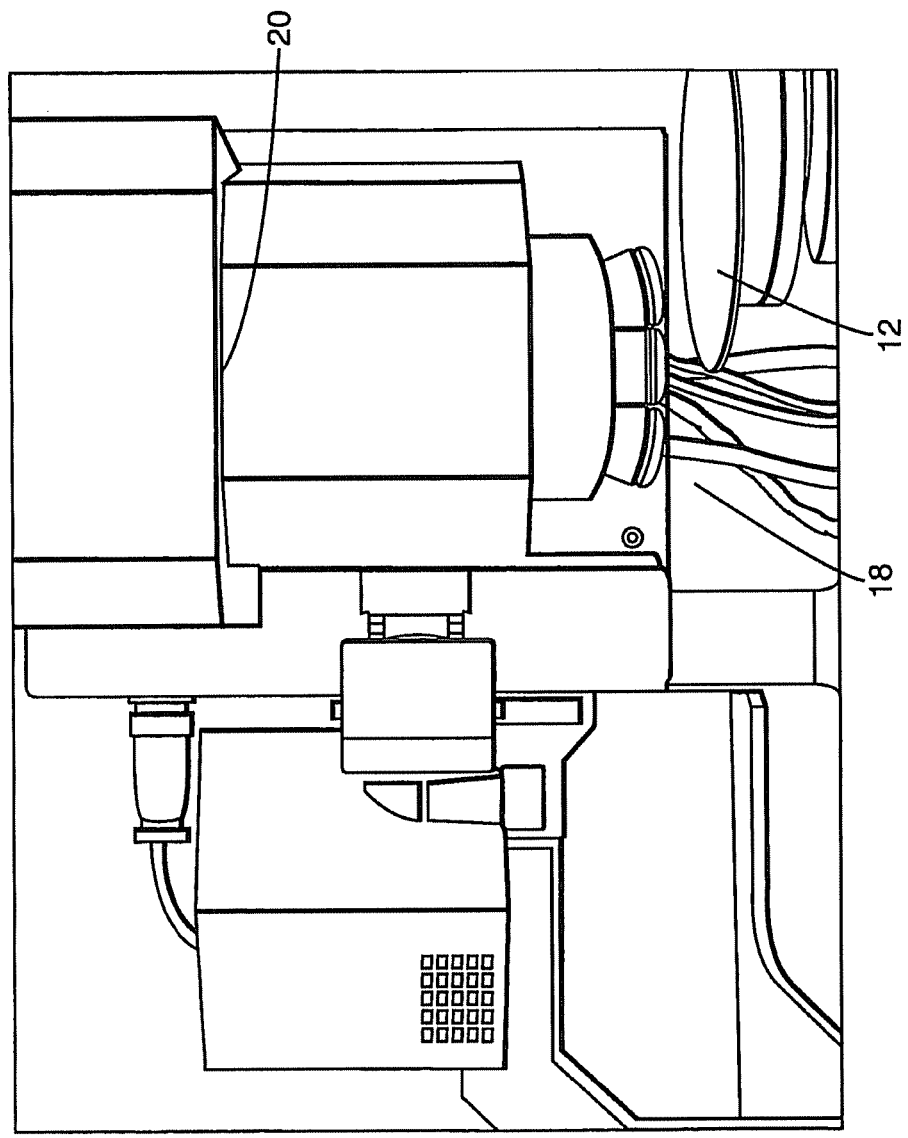
FIG. 13 is an enlarged view of the optics and wafer top plate.
Figure 14:
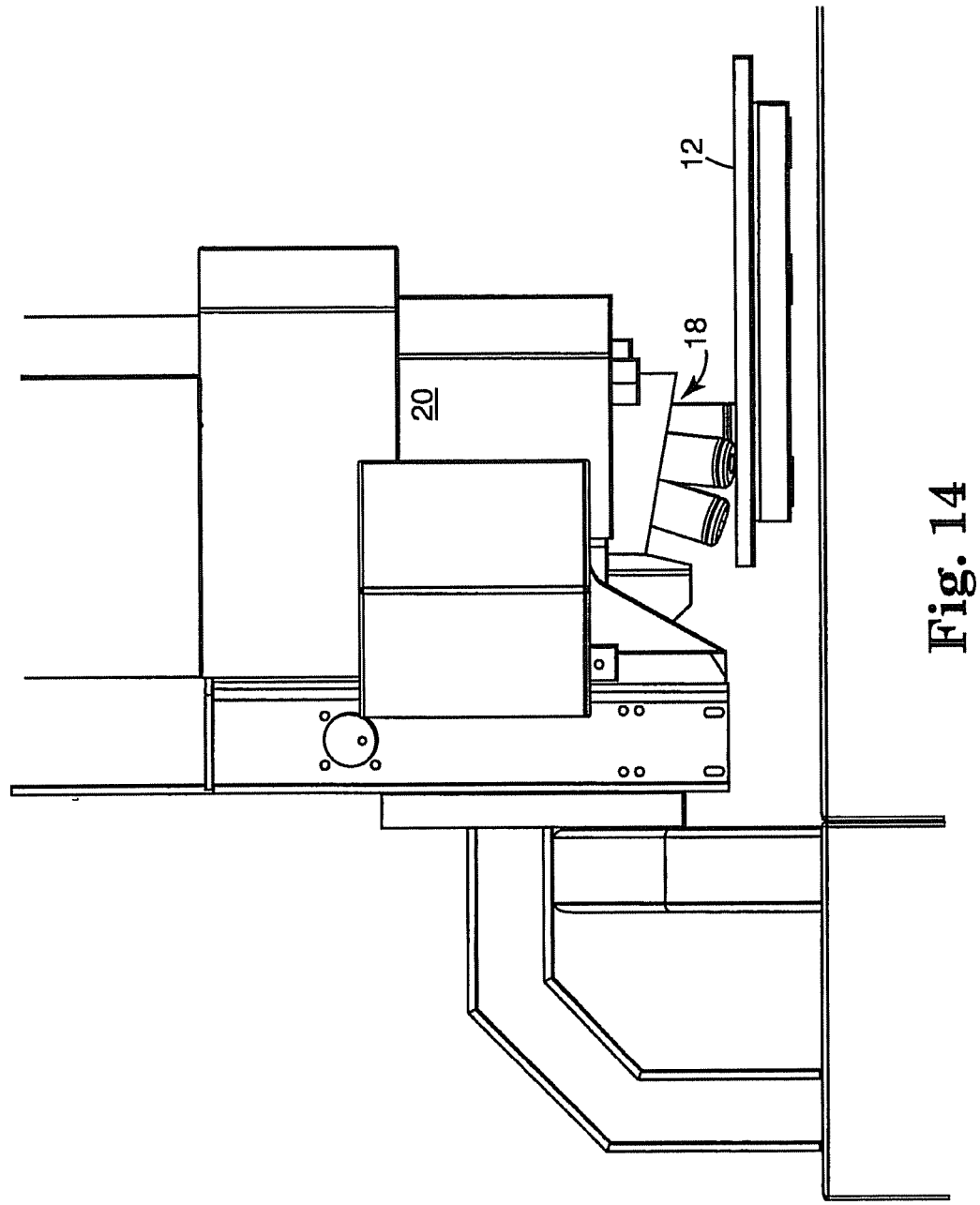
FIG. 14 is a side view of the wafer top plate and optics of FIG. 9.
Figure 15:
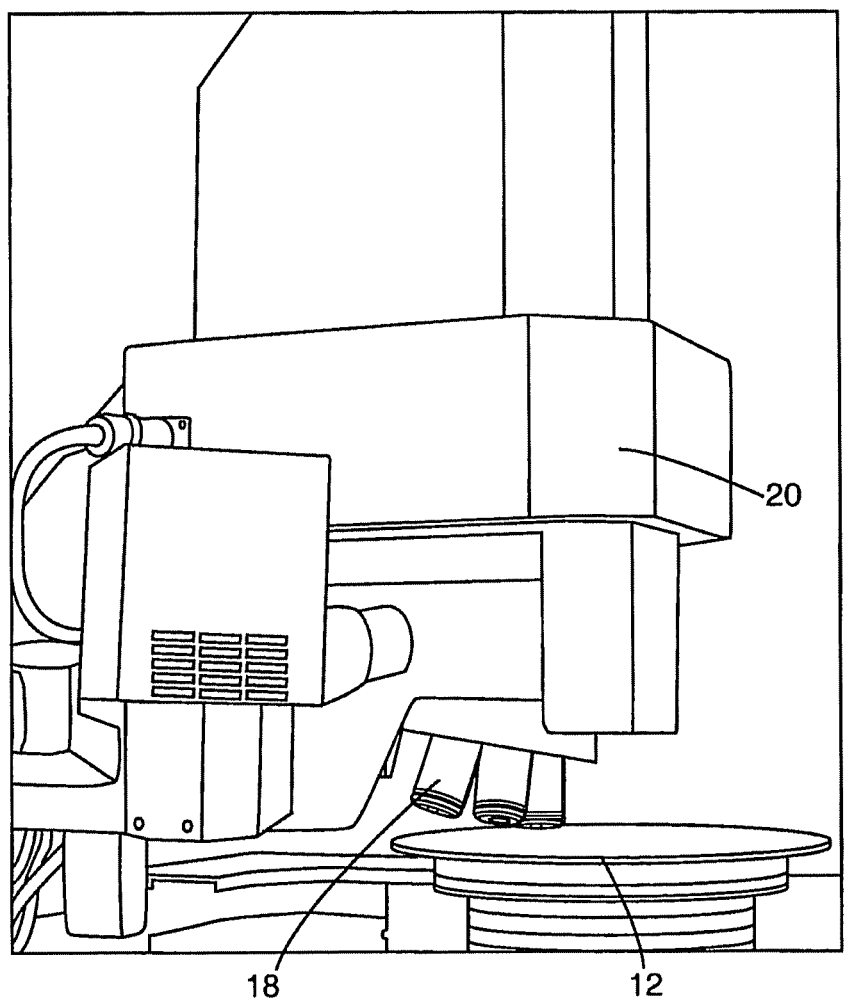
FIG. 15 is a left side perspective view of the top portion of the inspection station as shown in FIGS. 10-12.
Figure 16:
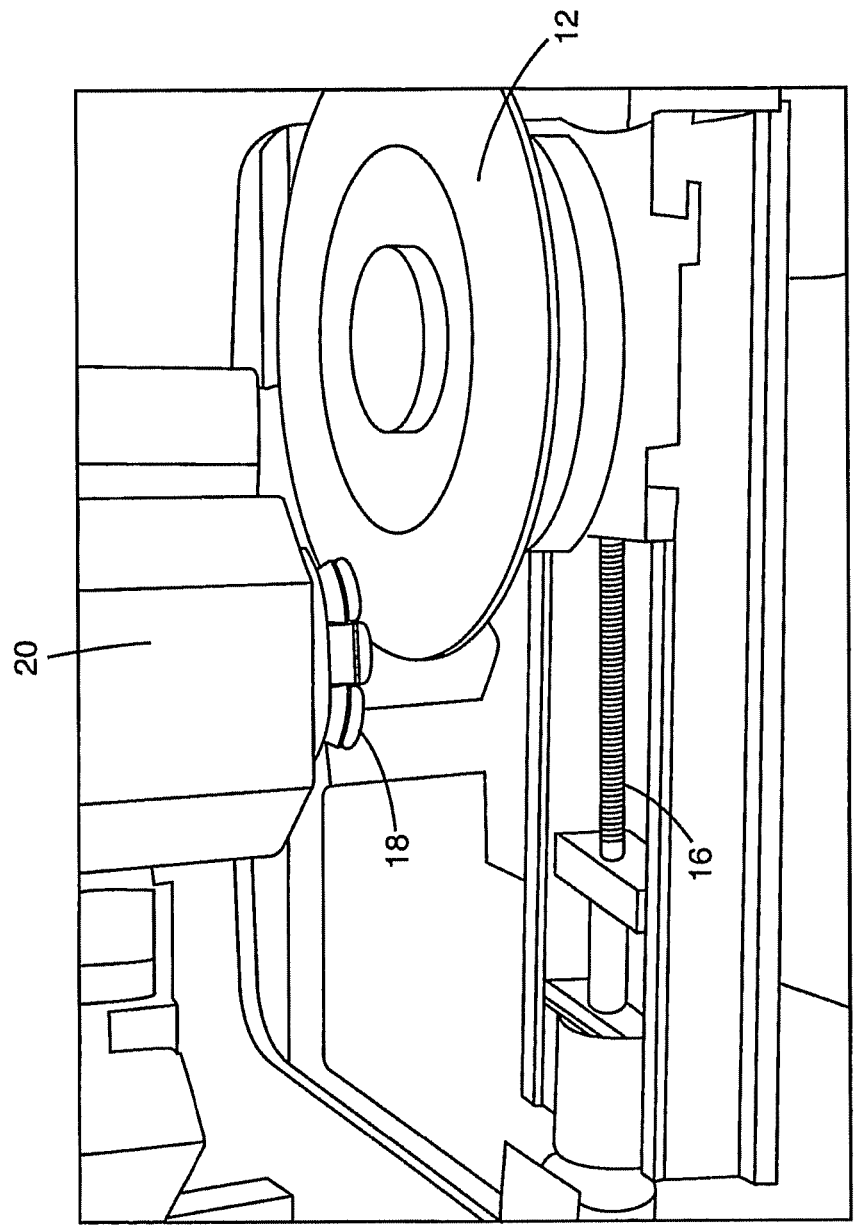
FIG. 16 is an enlarged view of one embodiment of the wafer top plate and the x, y and θ aligner.
Figure 17:
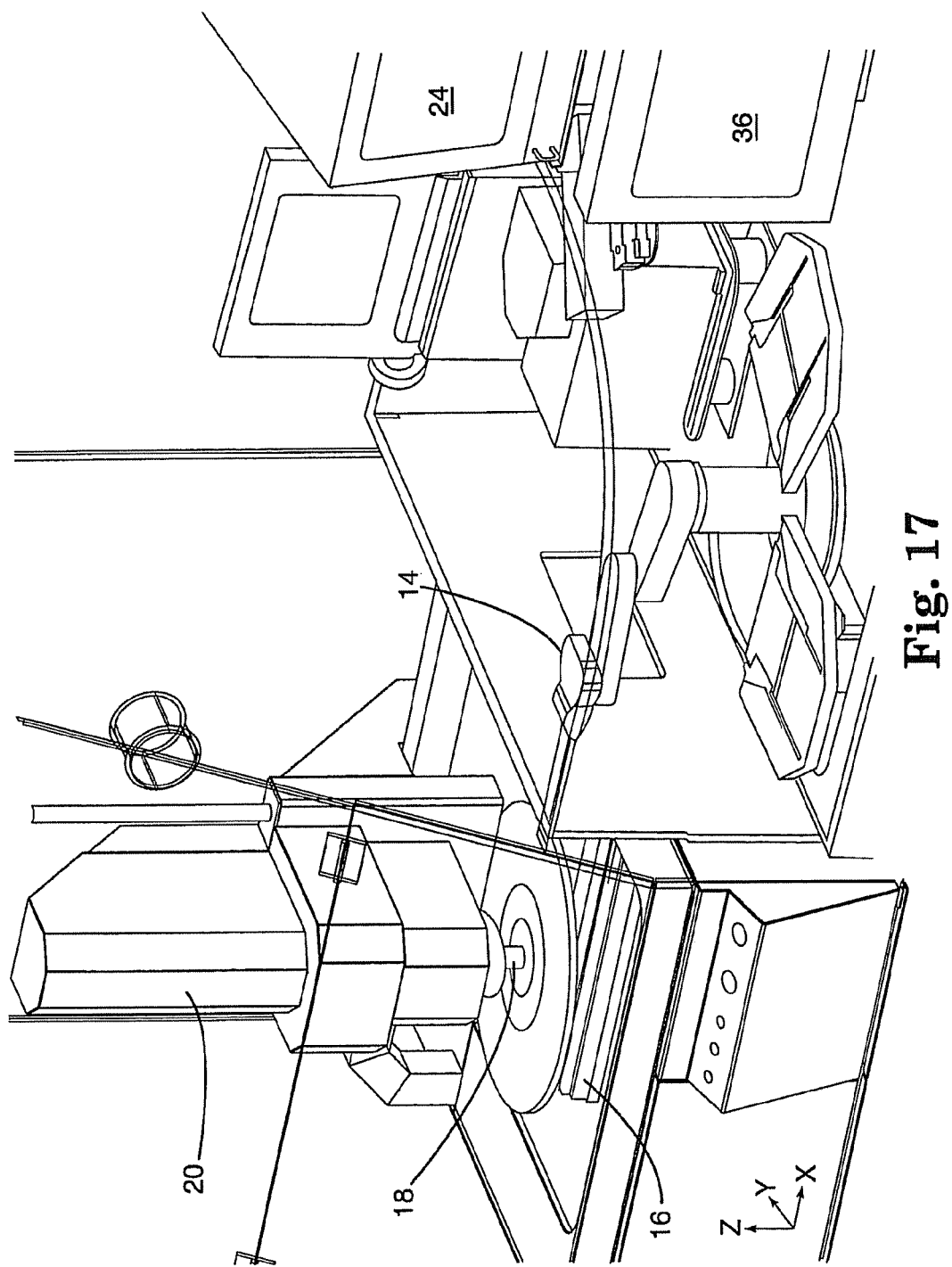
FIG. 17 is a partial perspective view of the top portions of the inspection and wafer handling stations.
Figure 18:
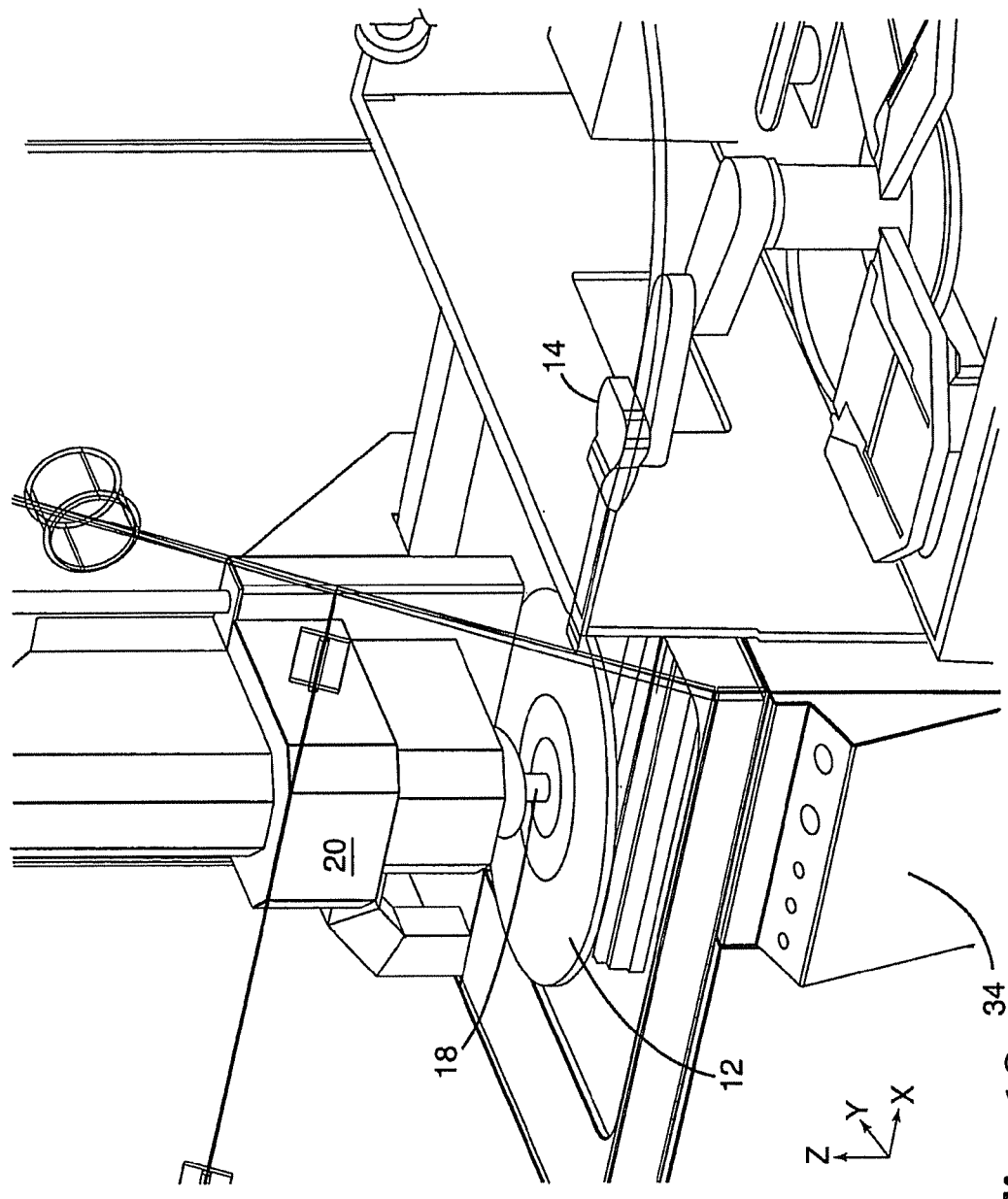
FIG. 18 is an enlarged view of the wafer handling and wafer top plate portions of the invention.
Figure 19:
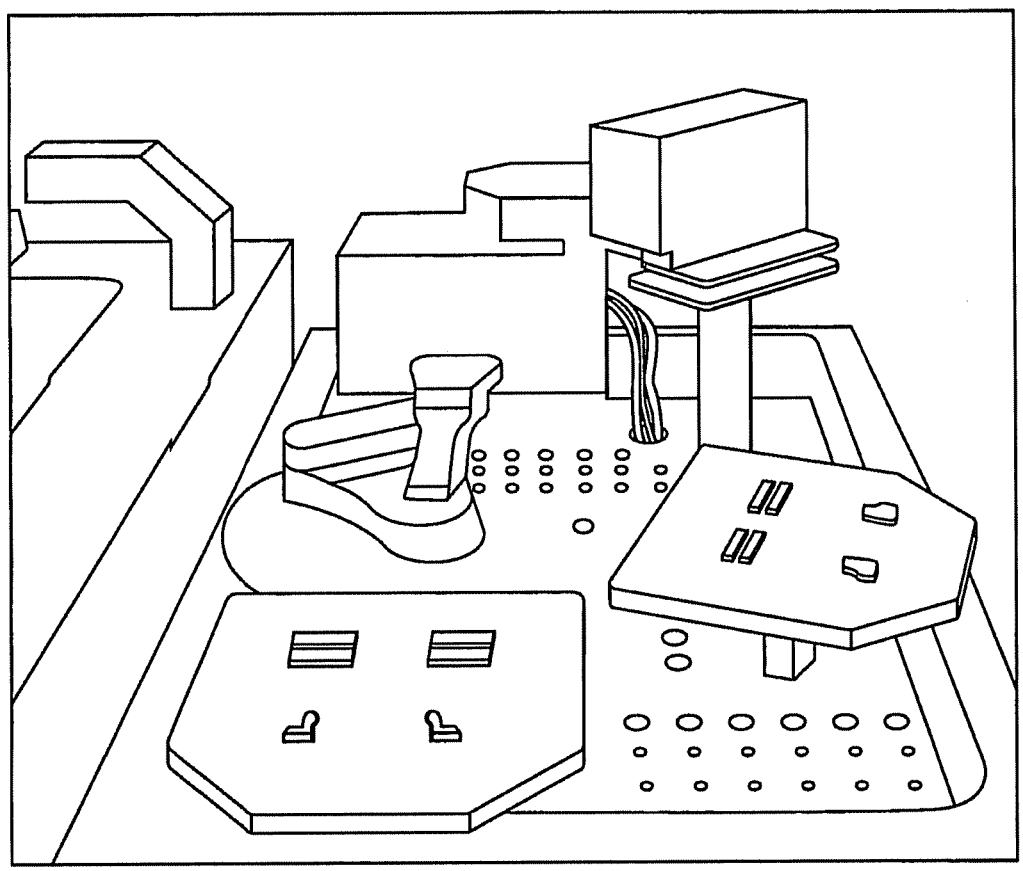
FIG. 19 is a side view of the wafer handling station.

The automated defect inspection system of the present invention is indicated generally at 10 as is best shown overall in FIGS. 1 and 8 (but in detailed portions in FIGS. 2-7 and 9-21) and is used in one environment to find defects on die on patterned wafers W but is intended for this and other uses including for inspecting whole wafers, sawn wafers, broken wafers, wafers of any kind on film frames, die in gel paks, die in waffle paks, MCMs, JEDEC trays, Auer boats, and other wafer and die package configurations (although hereinafter all of these uses shall be referred to generally as inspection of wafers W). The system inspects for many types of defects including, but not limited to, the following: metalization defects (such as scratches, voids, corrosion, bridging, etc.), diffusion defects, passivation layer defects, scribing defects, glassivation defects, chips and cracks from sawing, probe or bond area defects (such as missing probe marks, discoloration, missing metal and probe bridging), diffusion faults, vapox, etc. The system may also be additionally or alternatively used to inspect interconnects or bumps, such as gold or solder bumps, for defects or other characteristics such as size and shape.

Figure 2:
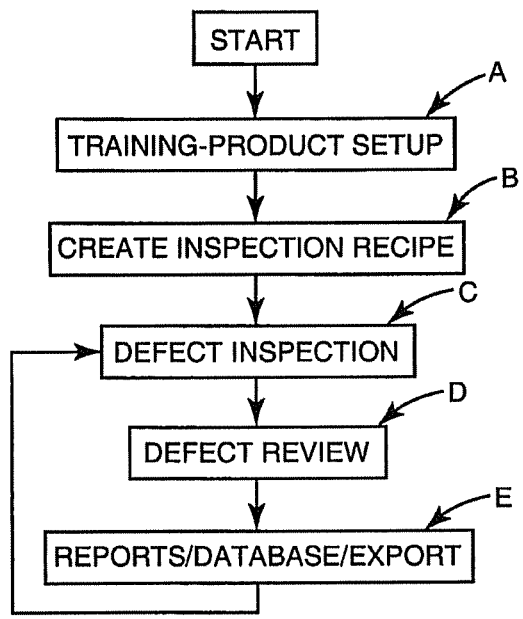
FIG. 2 is an overall flow chart of the process.
Figure 3:
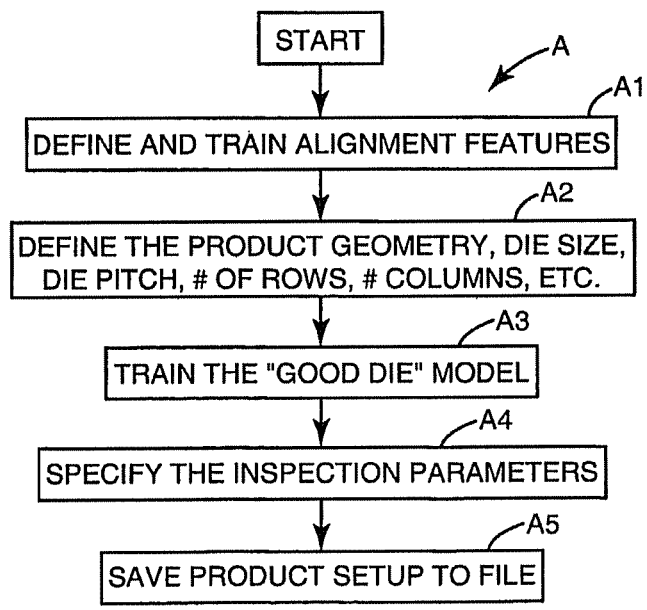
FIG. 3 is a more detailed flow chart of one step in the process as shown in FIG. 2.
Figure 4:
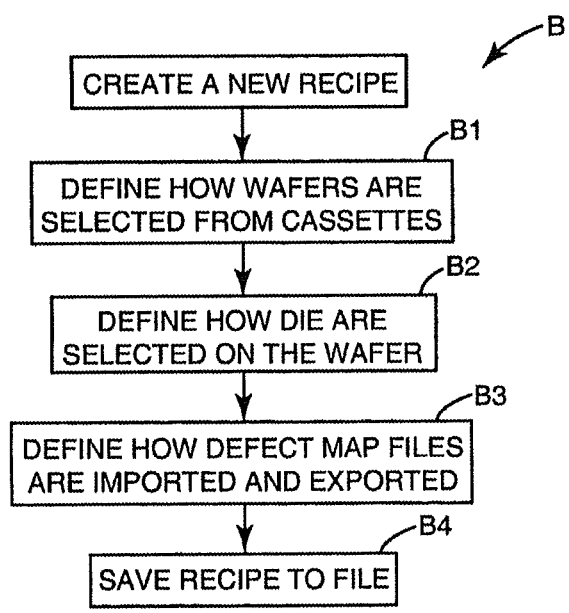
FIG. 4 is a more detailed flow chart of one step in the process as shown in FIG. 2.
Figure 5:
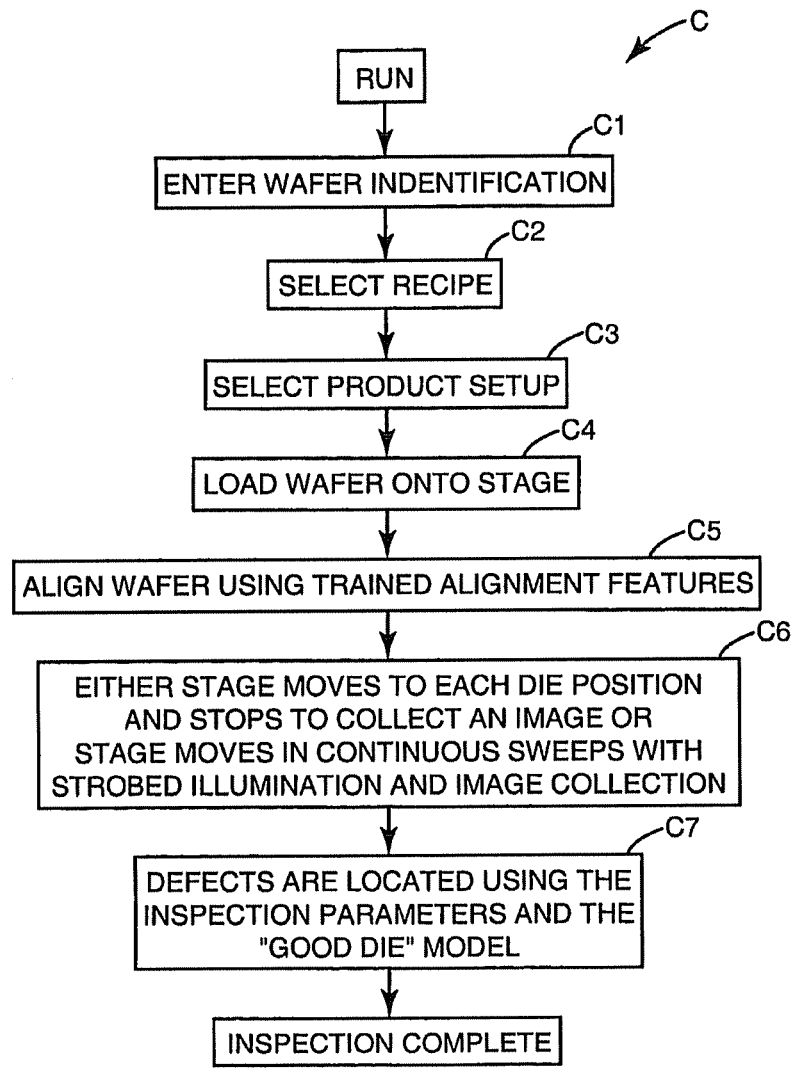
FIG. 5 is a more detailed flow chart of one step in the process as shown in FIG. 2.
Figure 6:
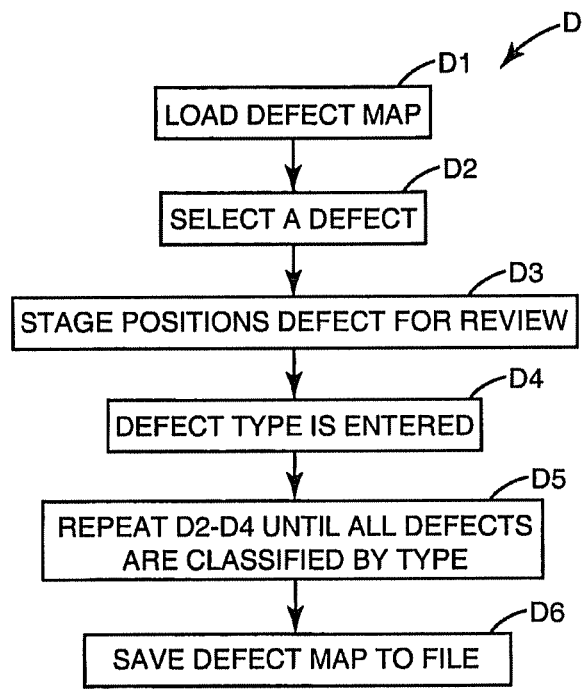
FIG. 6 is a more detailed flow chart of one step in the process as shown in FIG. 2.
Figure 7:
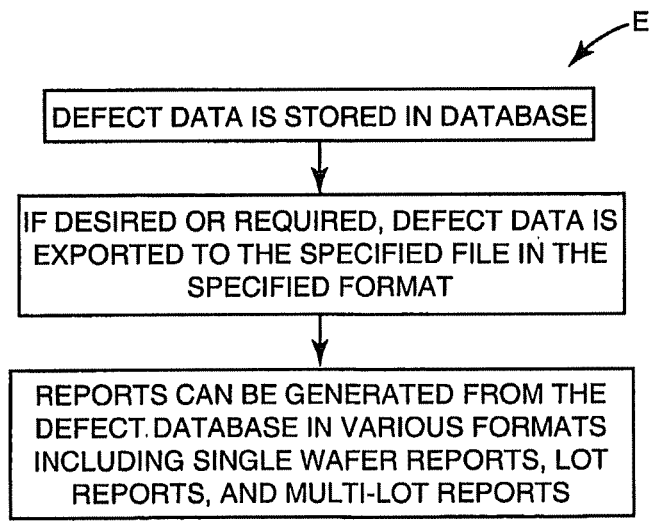
FIG. 7 is a more detailed flow chart of one step in the process as shown in FIG. 2.

The system and process encompasses, in general, a multiple step process as shown in FIG. 2 of training (step A) the system, creating (step B) an inspection recipe, inspecting (step C) die or wafers based upon this training and recipe, defect review (step D) if desired, and defect reporting (step E) if desired. The system 10 for performing this process includes, in general, a wafer test plate 12, means for providing a wafer to the test plate referred to as 14, a wafer alignment device 16 (x-y-θ or x-y-z-θ aligner) for aligning each and every wafer at the same x, y, and θ location or x, y, z, and θ location, a focusing mechanism 18, a camera 20 or other visual inspection device for visual inputting of good die during training and for visual inspection of other unknown quality die during inspection, a parameter input device 22 for inputting parameters and other constraints or information such as sensitivity parameters, geometries, die size, die shape, die pitch, number of rows, number of columns, etc., a display 24 for displaying the view being seen by the camera presently or at any previous saved period, a computer system 26 or other computer-like device having processing and memory capabilities for saving the inputted good die, developing a model therefrom, and comparing or analyzing other die in comparison to the model, a marking head, a frame 30, a hood 32, a control panel 34, and a system parameters display 36.

In more detail the system 10 and associated process are as follows. Training (step A) as initially displayed in FIG. 2 and shown in more detail in FIG. 3 involves (1) defining and/or training alignment features and parameters (and storing) in the computer system 26 for use during training where all of this is shown as step A1, (2) defining (and inputting into the computer system) the wafer and/or die geometries, the wafer and/or die sizes, the die pitch, the number of rows, the number of columns, etc., and storing all such information in the computer system 26 for use during training and/or inspecting where all of this is shown as step A2, (3) training the system as to what a "good die" comprises by aligning via device 16 and viewing via camera 20 a plurality of known good die and forming a model within computer system 26 to define what an ideal die should look like based upon the common characteristics viewed where all of this is shown as step A3, (4) setting inspection parameters which are values that indicate to the computer system 26 how close an unknown quality die must match the good die model to be considered a good die (that is, what differences from the exact model are tolerable to still be considered a good die) where all of this is shown as step A4, and (5) saving this training model and its features, parameters, etc. to the computer system 26 as shown by step A5.

Creating (step B) an inspection recipe involves creating a new recipe (if a previously defined recipe is to be used, then the creating step of B is skipped). Creating a new recipe involves (1) defining how wafers W are selected from cassettes or other storage receptacles where all of this is shown as step B1, (2) defining how the dies on each wafer W are to be selected for defect inspection where all of this is shown as step B2 (often dies are merely inspected in sequential or similar order; however, any other order may be defined), (3) defining how defect inspection map files are imported and exported where this is shown as step B3, and (4) save this recipe where this is step B4.

Inspecting (step C), referred to as defect inspection, involves (1) inputting a wafer identification code, if desired, and is referred to as step C1, (2) selecting a recipe that was defined in step B where this selecting is step C2, (3) selecting and inputting a product setup which is step C3, (4) loading a wafer onto the wafer test plate 12 using the wafer providing means 14 where loading is step C4, (5) aligning the wafer on the wafer test plate 12 using the wafer alignment device 16 for aligning each and every wafer at the same x, y, and θ location or x, y, z, and θ location and using the defined and/or trained alignment features and parameters of step A1, all of which is shown as step C5, (6) focusing the camera 20 onto the wafer W if needed, all of which is shown as step C6 (7) collecting an image of the wafer W using the camera 20 by moving the plate 12 to align the camera with a first die or other portion thereof, viewing and recording that die or portion thereof by opening the shutter and allowing the camera to view and record the image, moving the plate 12 to align the camera with another die or portion thereof, viewing and recording this another die or portion thereof, and repeating these steps until all of the die or portions thereof on the wafer that are desired to be viewed have been viewed and recorded, all of which is shown as step C7, (8) simultaneously during step C7, determining where defects are located on the given die being viewed based upon the "good die" model of step A3 and the tolerances of step A4, all of which is step C8, and (9) creating a defect map of the wafer W which is a collection of all of the images of all of the die including all of the defects found thereon, all of which is step C9.

Alternatively, step C7 may be replaced by the step of collecting an image of, the wafer W using the camera 20 by continuously moving the plate 12 so as to scan over all of the die on the wafer whereby the wafer is illuminated by a strobe light at a sequence correlating to the speed of the moving plate so that each die is strobed at the precise time it is under the camera 20. This allows for the continuous collecting of images without necessitating the stop and go procedure of aligning the camera with a first die, viewing and recording that die, moving the plate 12 to align the camera with another die, viewing and recording this another die, and repeating these steps until all of the die on the wafer have been viewed and recorded, etc.

Defect review D if and when it is desired (which is generally at the conclusion of defect inspection on a given wafer W since it is at this point that defect classification is often desired) involves (1) loading the defect map created in step C9, this reloading referred to as step D1, (2) selecting a defect to review (or alternatively reviewing all of the defects on the wafer in order) as step D2, (3) moving the plate 12 so as to position the wafer W such that the particular die with defect thereon is properly positioned under the camera 26, all of which is step D3, (4) user viewing and classifying of the defect such that user of the system 10 views and classifies the viewed defect, all of which is referred to as step D4, (5) repeating of steps D2-D4 until all of the defects that the user desires to review have been reviewed and classified as step D5, and (6) saving of classified defect map as step D6 as well as alternatively or additionally saving the defect information in any of a number of other formats for database or other management and review.

Defect reporting E if and when it is desired involves exporting or printing out the data stored in database format in step D6. This data may then be analyzed or otherwise used to perform statistical or other analysis on the types of defects, frequency of defects, location of defects, etc., which is useful to the wafer W manufacturers so as to allow them to focus on defect laden areas.

The above described steps and substeps are a basic explanation of the system and process of the present invention. The following description is a more detailed explanation of various parts and systems, and details of the steps these perform.

The wafer test plate 12 is a rotary stage that is equipped with a universal interface platform with vacuum, all of which provides a flexible interface for wafer, and die package fixturing. It is defined such that it quickly mounts and inspects; whole wafers, sawn wafers on film frame, die in gel pak, die in waffle-pak, MCM, JEDEC trays, Auer boats, and other wafer and die package arrangements and configurations.

The means for providing a wafer to the test plate referred to as 14 may be either manual in that the user moves the wafer from a cassette or magazine to the test plate 12, or automatic as is shown in the embodiment of the Figures. In the automatic environment, the wafer providing means 14 includes a robotic arm that pivots from a first position where a wafer W is initially grasped from a magazine or cassette to a second position where the wafer W is positioned on the wafer test plate 12 for inspection. After inspection, the robotic arm pivots the wafer W from the second position at the test plate 12 back to the first position where the wafer W is placed back in or on the magazine or cassette.

The robotic arm in the embodiment shown is a two part arm which has two sections, the first of which pivots about a center support and the second of which pivots about the end of the first. Surrounding the robotic arm in one embodiment is at least one cassette receiver (two shown in FIG. 1) which receives standard wafer transportation cassettes in which multiple wafers are stacked, an optional wafer pre-aligner which would provide a pre-alignment or rough alignment of the wafer, an OCR (optical character recognition) system, and the inspection station which includes the wafer top plate 12, x-y-θ aligner 16, optics 18, cameras 20, etc.

The wafer alignment device 16 for aligning each and every wafer at the same x, y, z, and θ location is a precision system of rotary motors, ball screws, direct or belt driven motors, worm or other gears, actuators, hydraulics, push rods, vacuums, or other mechanical or electrical equipment for moving the rotary stage either linearly or angularly to a precise desired location.

The same alignment mechanism and process is used during training as is used during inspection. Specifically in the embodiment shown, the wafer alignment device is a 2-D x, y and θ alignment process that is optionally coupled to a z height control. Specifically, it is in one example a 2-D x and y course alignment followed by a fine theta (θ) alignment process, all of which is coupled with and followed by a focus map process (using a previously generated height or focus map) for determining height or z and thus assuring the wafer is in focus. Basically, the course alignment uses a pattern located at the approximate wafer center which it has been trained to know and expect x and y location on thereby allowing it to find this pattern and x and y (2-D linear) orient the wafer as such to at least course align it This orientation is performed using the stage 12. Thereafter, fine alignment is performed by using a pattern near the perimeter of the wafer which it has been trained to know to get the θ (rotational) alignment correct. This is also performed using the stage 12. In both cases, the camera finds the pattern and the alignment mechanism moves the wafer until it is aligned.

The focus map or z orientation is performed by adjusting the camera and/or camera arm distance prior to focusing as is described below, and/or by changing objectives, and/or by focusing the camera. The adjustment that is performed is based upon a height map of the wafer from which focus is defined using pre-programmed points on the wafer.

The focusing mechanism 18 is an optical imaging mechanism with multiple optics therein for using different inspection resolutions. A motorized microscopic turret allows for selecting of the imaging optics from the multiple choices. For instance, a number of optics, such as three or five optics, may be supplied and typical choices include 1.25×, 2.5×, 5×, 10×, 20×, 50× and 100× objectives although any other objective is contemplated. The motorized microscopic turret and discrete objectives provide the means to select the optical magnification.

The camera system 20 or other visual inspection device is for visual inputting of good die during training and for visual inspection of other unknown quality die during inspection. The camera system may be any type of camera capable of high resolution inspection. An example of one part of such a camera system is a 3-CCD inspection camera used to capture die or other images during defect analysis.

One example of camera system 20 that is contemplated by the present invention is a two (2) camera system where one camera is an inspection camera and the other is a viewing camera. The inspection camera is a high resolution CCD camera that provides high resolution gray-scale images for inspection. The viewing camera is a high fidelity color image camera for visual review of found defects in, for example, 758×582 pixel resolution or alternatively 1008× 1018 pixel resolution or other known pixel sizes. In addition, the viewing camera provides high quality color images for operator defect review.

Computer controlled optics are provided that use long working distance microscopic objectives so as to provide for low distortion images that are required for accurate defect detection. Multiple magnifications may be automatically selected based on the user defined inspection recipes as described below.

Computer controlled illumination is integrated into and with the inspection camera and optics to complete the wafer imaging process. Alternatively, the illumination system may be coupled to the camera and optics so long as the illumination system works in conjunction with the camera. In a strobing environment as described herein, the illumination flashes or strobes on and off while the camera is continuously open whereby the strobing of light creates a plurality of differing images as the continuously operating camera passes over the substrate. In a non-strobing environment, the illumination is typically continuous or as needed while the camera shutters, that is opens and closes its viewing aperture such as via in one example a high speed electronic shuttering mechanism, as is needed to capture each desired image on the substrate.

Illumination may be by any known illumination means such as high intensity lights, lasers, fluorescent lights, arc discharge lamps, incandescent lamps, etc. The angle of the illumination may be of a brightfield only, darkfield only, or both brightfield and darkfield variety.

Brightfield illumination involves illuminating the substrates from above where the illumination system is typically adjacent to or part of the camera which is mounted directly above the substrate, that is at approximately a 90° or so orientation to the substrate as shown in FIG. 1. In the embodiment shown, the brightfield illuminator is adjacent to the camera and functioning in unison therewith. This brightfield illumination is very effective in illuminating flat or relatively flat objects on a substrate as the light is reflected generally back to the camera. In contrast, 3-d objects on the substrate will angularly reflect the light causing the light to be angled away from the camera. As a result, flat objects appear bright to the camera while 3-d objects appear dark.

Darkfield illumination is often used in conjunction with the brightfield to "brighten" the 3-d objects, or in the alternative to only brightly see the 3-d objects. The darkfield light is provided at low angles to the wafer top plate 12. The darkfield illumination works inverse of the brightfield in that it reflects light up to the camera at an angle, such as any angle between approximately 10° and 90°, to the substrate when the darkfield light is introduced to 3-d object on the substrate at an angle rather than from directly above as in brightfield illumination, while reflecting light at an angle along the periphery opposite the light introduction where the object is flat. Darkfield light thus brightly illuminates 3-d objects while not illuminating flat objects very well.

In one embodiment of the present invention, two darkfield options are available, namely a high angle darkfield illumination and a low angle darkfield illumination. The high angle darkfield illumination is provided in one embodiment at an angle between approximate 10° to approximate 80° between the brightfield illumination provided from directly above the substrate (perpendicular to the substrate) to the low angle darkfield illumination provided at almost a parallel angle to the substrate. High angle darkfield illumination may be provided by any of a number of light sources including all of those listed above describing general illumination; however, in one embodiment the high angle darkfield illumination is either a ring light, or a fiber optic bundle providing light angled toward the substrate at approximately a 45° angle.

Figure 20:
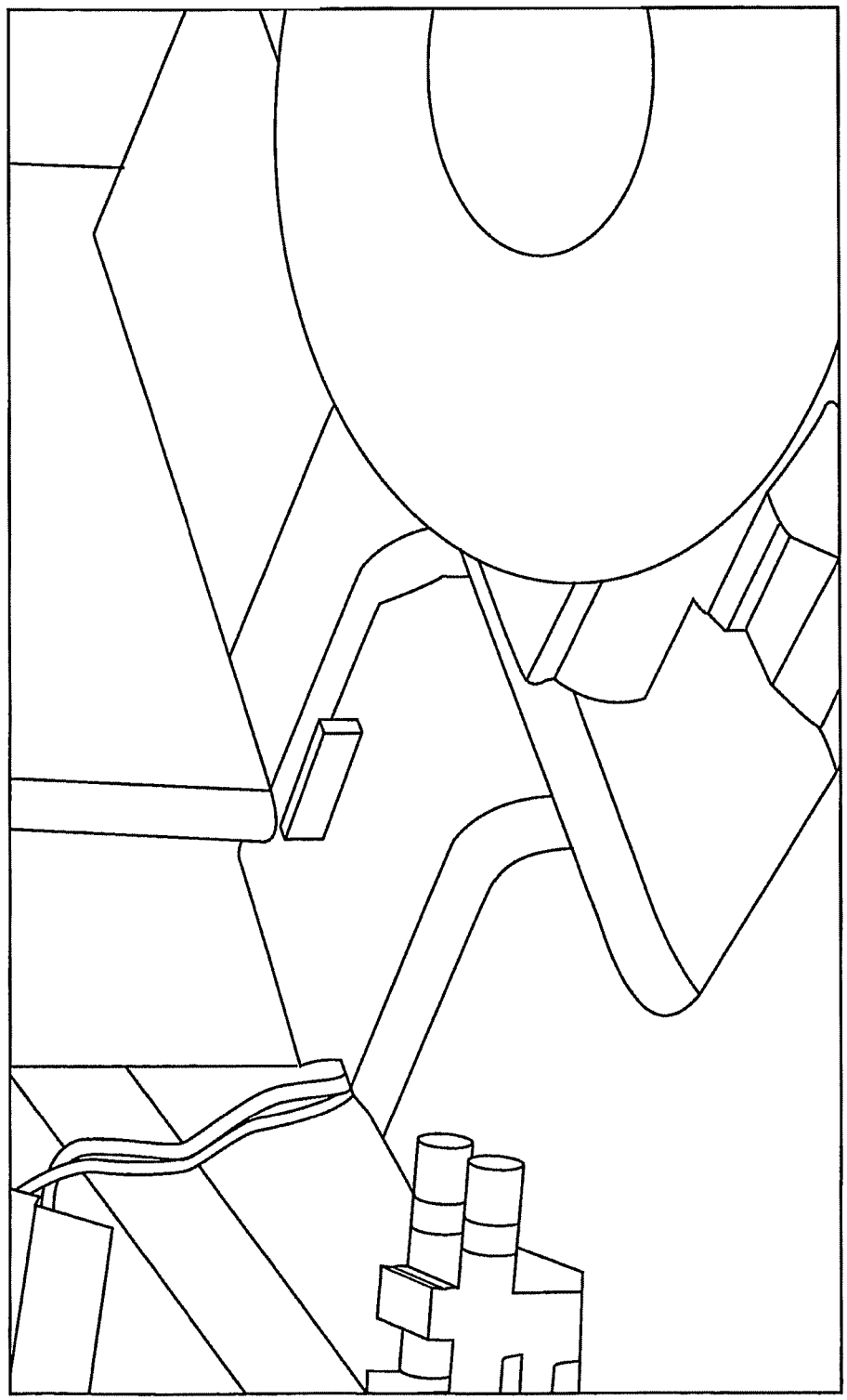
FIG. 20 is a partial view of the darkfield option of the present invention.
Figure 21:
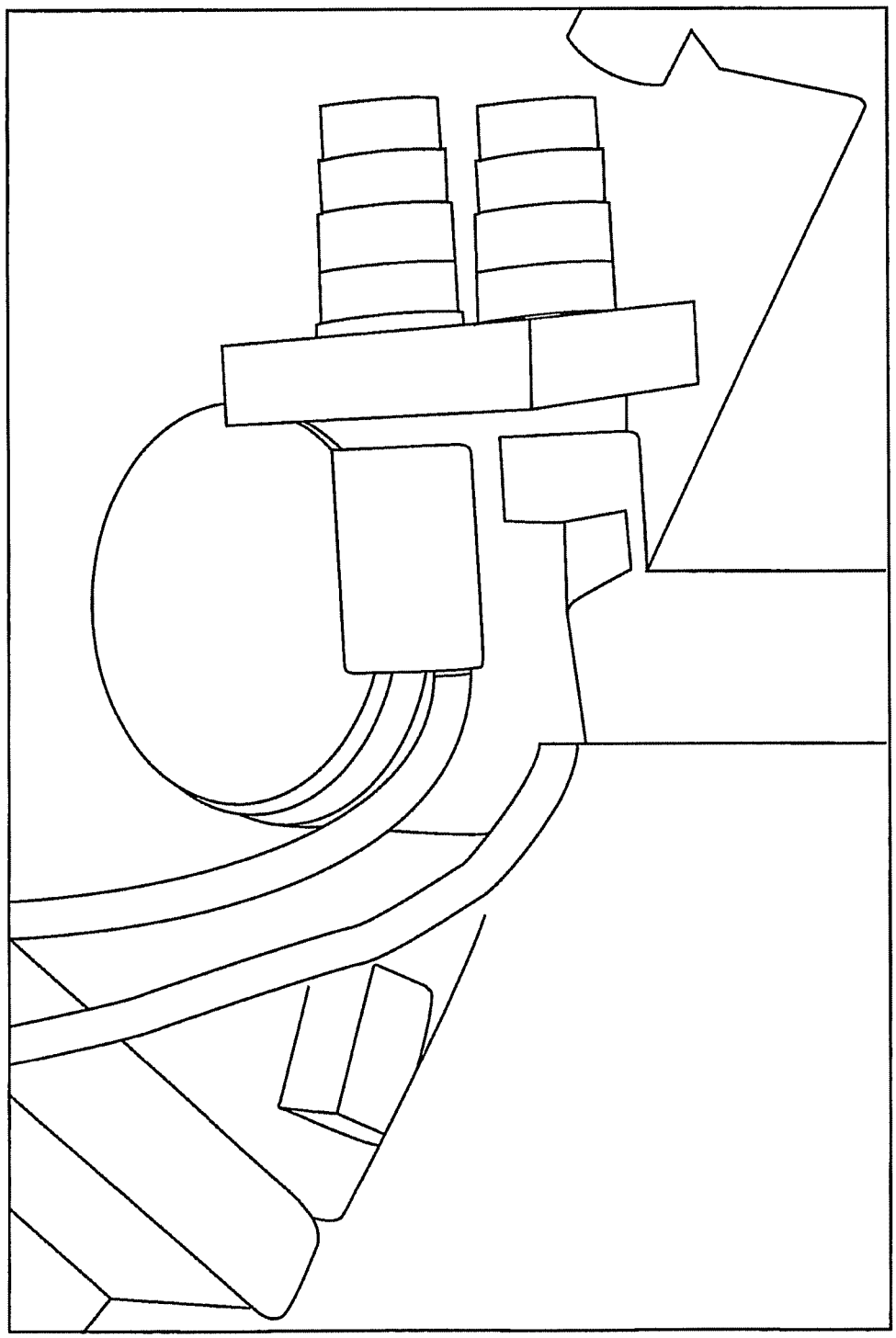
FIG. 21 is an enlarged view of the darkfield lasers of the darkfield option.

The system 10 with a low angle darkfield option as shown best in FIGS. 20-21 to include a plurality of illuminators spaced about the periphery. In one example four illuminators are used and each is equally spaced from the other at a 90° separation. In another example (FIGS. 20-21 where one pair are shown), eight illuminators are used at a 45° separation, and in an alternative associated therewith and shown in the drawings, the illuminators are teamed up in pairs at 90° separation to double the capacity of the illuminators at a given angle. In the embodiment shown, the low angle darkfield illuminators are lasers. In this embodiment, the lasers provide darkfield light at low angles to the wafer top plate 12. Specifically, the angle between the laser beam focused on a focal point of the substrate and the general planar nature of the substrate is low or minimal, such as less than 10°. As a result, the darkfield illumination emitted from the laser reflects off of the substrate and up to the camera at an approximate 80° to approximate 90° angle to the substrate, and preferably approaching approximately 90°, when the darkfield light is introduced to the 3-d object, such as a bump, on the substrate.

The user, where the system is equipped with both brightfield and darkfield illumination, has the option of using one or the other or both. This provides significant options. For instance, if the inspection is being performed on die that tend to only have flat objects thereon, brightfield illuminates these objects well and is more than sufficient for this type of inspection. Alternatively, if the inspection is being performed on die that tend to have 3-d objects, then darkfield may be sufficient. However, as in many cases, such as with gold bumps which are generally very flat but very rough and tend to include 3-d nodules protruding therefrom, a combination of the two is often beneficial. In this example, the brightfield illumination indicates the presence of any defects such as scratches, etc., and the presence of the bump while the darkfield illumination shows the nodules and rough surface on the bump. Without the darkfield, the bump shows up as a dark image. Once darkfield is introduced, the nodules are located as white spots on the bump.

Darkfield also assists in defect classification because brightfield light does not differentiate between a particle or defect that extends from the surface versus one that is embedded or scratched into the surface. Darkfield illumination does differentiate these extending versus embedded defects.

In one embodiment, the system 10 includes a brightfield illumination system that is physically located adjacent to or incorporated physically into the camera so as to provide brightfield illumination from above the objects illuminated. In another embodiment, the system 10 includes a darkfield illumination system that is located peripherally around the wafer top plate 12 at low angles of difference from the top plate, angles such as 1° to 10°. In an even further embodiment, both brightfield illumination from above the object and darkfield illumination from around the periphery of the object are provided. As indicated above, the illumination as provided by the brightfield and darkfield illumination systems may be provided by any known illumination source such as a white light source such as incandescent, fluorescent, or other similar gas envelope or similar electrical lights, or by lasers or similar devices.

The parameter input device 22 is for inputting parameters and other constraints or information. These parameters, constraints and information include sensitivity parameters, geometry, die size, die shape, die pitch, number of rows, number of columns, etc. It is contemplated that any form of input device will suffice including a keyboard, mouse, scanner, infared or radio frequency transmitter and receiver, etc.

The display 24 is for displaying the view being seen by the camera presently or at any previous saved period. The display is preferably a color monitor or other device for displaying a color display format of the image being viewed by the camera 20 for the user's viewing, or alternatively viewing an image saved in memory. This monitor, or another adjacent or other monitor may be used to view the gray-scale inspection image of the camera 20 that is being used by the system 10. This display 24 is used during inspection to show the image being viewed by the camera 20. In addition, the system parameters display 36 is also available for displaying other information as desired by the user such as system parameters.

The computer system 26 or other computer having processing and memory capabilities is for saving the inputted good die, developing a model therefrom, and comparing or analyzing other die in comparison to the model based upon defect filtering and sensitivity parameters to determine if defects exist. The computer system 26 is also used to perform all other mathematical and statistical functions as well as all operations. In one embodiment, the computer system 26 is of a parallel processing DSP environment.

The marking head is provided for marking a particular die such as a defective one. In one embodiment, the marking head is a die inking mechanism. It is used whereby each die may be inked after inspection, or all defective die may be inked, or all defective die may be inked after review and/or classification, etc. Inking may also be used in a "forced inking" manner whereby pre-specified die are inked regardless of electrical or visual inspection such as all die at the edge of the wafer.

An air knife is optionally provided for cleaning the wafers prior to inspection. The air knife is basically a conduit of some design through which air may be injected where the conduit includes one or more orifices or outlets. The air is projected out of the orifices which are selectively positioned on the conduit and in relation to the wafer so as to blow dust and other particles off of the wafer prior to review. This helps to eliminate false defect determinations.

These systems and parts are part of system 10 and are used to perform the defect inspection. This defect inspection is briefly described above, and is now described below in detail.

The overall training step A is described below in more detail.

The step A1 is defining and/or training alignment features and parameters (and storing) in the computer system 26 for use during training. This alignment technique, when performed in step A3 and C5 as described below to define a good die and to inspect, is a two function process, namely a physical alignment and an image alignment. At this point we define what parameters are to be used during the physical and image alignment. These parameters include defining markers as are needed during physical alignment, and distinct elements and buffers as are needed during image alignment. The actual physical and image alignment steps occur during step A3 and C5 as described below.

The step A2 is defining (and inputting into the computer system) the wafer and/or die geometry, the wafer and/or die sizes, the die pitch, the number of rows, the number of columns, etc., and storing all such information in the computer system 26 for use during training and/or inspecting.

The step A3 is training the system as to what a "good die" comprises by aligning via device 16 and viewing via camera 20 a plurality of known good die and forming a model within computer system 26 to define what an ideal die should look like based upon the common characteristics, elements, ranges, etc., viewed. A good die is defined as a die that does not have defects but may very well and is actually likely to have process variations in it; however all of these process variations have been deemed not to be defects and rather to be acceptable variations. Preferably, the entire or full spectrum of acceptable random deviations is supplied by this training set of typically twenty, thirty or up to one hundred good die that are shown to the system during training, although no minimum (however, definitionally at least two are required to meet the definitional requirements of a mean and standard deviation) or maximum is required. However, the larger the pool the more accurate the results because a better, more diverse model is created. Thus color drifts and contrast shifts as well as many other deviations would be part of the training set. Basically, the system 10 performs die inspection by studying a user-provided set of known good die.

The alignment may involve either physical alignment or image alignment, or both. Physical alignment basically involves inputting specific location markers on or around each wafer, die or sub-section of die which are used as location points from which the wafer and die are located and aligned. At step A1, these markers were defined.

Physical alignment involves the wafer test plate 12 via the wafer alignment device 16 aligning each and every wafer, die, etc., in the same x, y, and θ location by looking for and aligning with these location markers. In use, the system takes an overall picture or image of the wafer, die or sub-section thereof and looks for the specific location markers. The system uses a hunting method to find the markers. Once one or more specific location markers are identified, and it is found that the markers are in some other location or orientation than expected, then the wafer test plate 12 spins, turns, adjusts or otherwise moves in a translational or rotational manner in the x, y, and θ directions the wafer, die or sub-section.

The system also may perform image alignment. During step A1, distinct elements and buffers, as are needed in image alignment, were defined.

This image alignment may also be referred to as software alignment as the software actually performs the alignment by aligning the image that is taken rather than physically moving the wafer or die. This image alignment is performed on each section of the wafer, such as each die, during one or both the good die modeling and the unknown quality die inspecting. It is often necessary because each image taken may be off slightly in comparison to adjacent images or to a common location on another wafer. The actual process of image alignment basically assures that all images taken of a particular location will align, that is when overlapped the features of the images will align, rather than have an offset or twist, so that only defects stick out.

Image alignment, when performed as needed in steps A3 and/or C5, involves the camera looking for a distinct element on the die from which to turn or move the image to "square" it up. The distinct element is generally an element large enough that defects therein will not be an issue. The element also must be of a distinct shape. If the distinct element is where we expect it to be then the image lines up and no image alignment is necessary; however, it is not, then the distinct element must be found and the image adjusted.

The hunting for the distinct element in image alignment may be performed on the entire die. However, this is expensive and time consuming. As a result, smart alignment may alternatively be performed.

With smart alignment, a buffer is defined into the image. This buffer allows for "wiggle", that is movement or twisting in the image. This buffer is typically an x amount and a y amount of movement that is expected. This buffer is then used to define the area around the expected location of the distinct element to be searched for the distinct element. Once the distinct element is found, then the x and y distance that the distinct element is off from the expected distinct element location is the distance the entire image is moved in the x and y direction to align the image.

The viewing encompasses collecting an image of the wafer W, a known good wafer, using the camera 20 by moving the plate 12 to align the camera with a first image which may be the whole wafer, a part of the wafer, a die, or a part of a die and then viewing and recording that image. Thereafter moving the plate 12 to align the camera with another image, viewing and recording this another image, and repeating these steps until all of the images on the wafer have been viewed and recorded. An alternative step C8 involves continuous motion and strobe illumination as is described below. In either case, this is then repeated for a plurality of known good die or wafers as viewing of a pool of wafers is necessary to form a model of a good die.

The actual defect inspection algorithm is calculated from the collection of images of the set of "good die". An image or images are taken of each good die in a set of good die. Each image is composed of pixels such as for example an approximately one thousand by one thousand (1000×1000) array or grid of pixels, although any number may be used. For each same pixel on all of the good die images, that is for each common x,y coordinate, which is a pixel, a mean and standard deviation is calculated of the pixel value, that is the gray-scale value of that given pixel. So in a grouping of 30 good die, as used as an example above, where each die is an array of 1000×1000 spots (1 million total spots) each referred to as a pixel, a mean and a standard deviation of the gray-scale number for each pixel at x,y coordinate 1×1, 1×2, 1×3 and so on all the way to 1000×1000 is calculated; that is a mean and standard deviation is calculated for pixel 1×1 using the gray scale measurement for pixel 1×1 on all 30 die, and so on for each of the 1 million die.

In one embodiment, the gray scale numbers for each pixel, are used to calculate the mean and standard deviation, and these are in a range. One example is a 256 scale scheme, where one end, such as 0 in the 256 scale scheme, represents a dark or black colored or shaded image and the other end, such as 255 in the same 256 scale scheme, represents a white colored or shaded image.

The collection of all of the means, that is for all of the pixels, for a type of die is in effect the perfect die of that type and in essence defines the good die model. The collection of all of the standard deviations, as adjusted as described below for sensitivity and filtering, for a type of die is in effect the allowable range inside of which the die is deemed good, and outside of which the die is questioned as to defects.

The step A4 is setting inspection parameters which are values that indicate to the computer system 26 how close an unknown quality die must match the good die model to be considered a good die (that is, what differences from the exact model are tolerable to still be considered a good die). Several such inspection parameters are defect sensitivity, minimum defect contrast and defect filtering.

In the embodiment shown defect resolution is dependent upon the optical magnification. Selecting a higher magnification results in a smaller field of view of the image. The magnification selected may result that multiple images are required to inspect a single die or that many can fit in a single image. The die size and optical magnification are inputted in step A2. It is however noted that smaller defect resolution results in more imaging per die and thus additional time to defect inspect the same quantity of die. Alternatively, a camera with adjustable resolution may be implemented whereby this adjustment feature would control sensitivity rather than image size.

Defect sensitivity involves user defined multiplication factors of the mean and standard deviations calculated to define the known good die model as described above. Defect sensitivity is described below in more detail in step C7.

Minimum defect contrasting involves user defined absolute limits on the upper and lower limits defined from the mean and standard deviation. Minimum defect sensitivity is also described below in more detail in step C7.

Defect filtering involves statistical or data filtering including area, size, region of interest and/or clustering filtering, as well as connection and/or reduction factor filtering. This filtering allows the user to filter out items that appear as defects but are not in critical areas, of sufficient size or shape or are otherwise acceptable and thus desirable to not be labeled as defects. In the embodiment shown, defect filtering is provided for each inspection recipe or round. This allows the system performance to be optimized for the user's application. The defect filtering feature uses defect position and geometry information such as shape, size, x-y coordinates, etc., to automatically determine if the defect requires further review and classification by the operator. An example is as follows, any defects above a certain size may be determined to be positively defects not subject to further review. In addition or as an alternative, any defects below a certain size are filtered out as not being a defect although being outside of the "good die" model. There may also be an area in between that requires operator review at the review steps of step D4. Similarly, shapes, positions, configurations, arrangements, etc., of anomalies from the "good die" model may be filtered. Defect filtering is further defined below.

The step A5 is saving this training model and its features, parameters, etc., to the computer system 26.

The overall inspection recipe creating step B involves creating and storing an inspection recipe for each type of item, that is wafer, die, etc., to be inspected. An unlimited number of inspection recipes can be created, copied and edited so as to allow the user to customize the inspection process.

The step B1 is defining how wafers W are selected from cassettes or other storage receptacles. The step B2 is defining how the dies on each wafer W are to be selected for defect inspection. The step B3 is defining how defect inspection map files are imported and exported. The step B4 is saving this recipe.

The overall inspecting step C, referred to as defect inspection, is an advanced proprietary digital image analysis technique for semiconductor wafer inspection. The system performs wafer inspection after first studying a user provided set of known good die as described above in step A3. This method of learning and inspecting is more powerful than traditional template or model matching inspection. It is noteworthy that even random variations in a known good die may be determined to be acceptable which is not the case with traditional template or model matching. In effect, this robust approach to wafer inspection functions similar to a human operator without the fatigue and other problems.

The step C1 is inputting a wafer identification code if desired. This is required where wafer mapping is to occur because this provides a way to identify each wafer for later review of defects, etc. The wafer identification code may be of any known identification system such as alphanumeric characters, bar codes, 2-D matrix codes, etc.

The step C2 is selecting a recipe that was defined in step B. The step C3 is selecting a product setup if one is desired.

The step C4 is loading a wafer onto the wafer test plate 12 using the wafer providing means 14. Loading onto the wafer test plate may be either by manual loading or using an automatic system where wafer with die thereon are automatically transferred from a cassette or magazine into the inspection area. The automatic system allows for elimination of all manual handling.

The step C5 is aligning the wafer on the wafer test plate 12 using the wafer alignment device 16 for aligning each and every wafer at the same x, y, z, and θ location and using the defined and/or trained alignment features and parameters of step A1. This has been described above in detail as the same process of physical alignment and image alignment is used here as was used to align the known good wafers to form the good die model.

It is often also necessary to focus the camera 20 onto the wafer W if it is not already focused. This occurs, if needed, during or after step C5 and is the z orienting of the wafer which is defined by a height map.

The step C6 is collecting an image of the wafer W using the camera 20 by moving the plate 12 to align the camera with a first image which may be the whole wafer, a part of the wafer, a die, or a part of a die and then viewing and recording that image, and thereafter moving the plate 12 to align the camera with another image, viewing and recording this another image, and repeating these steps until all of the images on the wafer have been viewed and recorded. An alternative step C6 involves continuous motion and strobe illumination as is described below.

The step C7 is simultaneous with step C6 and involves determining, where defects are located on the given die being viewed based upon the "good die" model of step A3 and the tolerances or parameters of step A4. Basically, each pixel on the unknown quality wafer is viewed whereby defect sensitivity and filtering are used in conjunction with the "good die" model to determine if the pixel and/or any group of pixels are deemed "good" or questionable.

Initially anomalies or differences between the "good die" model and the image are spotted and then sensitized and filtered. To simplify the determination, an upper level and lower level value is determined for each pixel on each die, based upon the mean and standard deviation calculations as well as the user defined sensitivity and absolute limits. The viewed image is then filtered using one or more of a variety of filter techniques including connection factoring, reduction or noise reducing factoring, and statistical or data filtering on, blob identification such as area, size, region of interest, and/or interactive filtering. After filtering, the questionable defect areas are identified. Basically, defect sensitivity and minimum defect contrast are used to define the upper and lower level values which are in effect the adjusted standard deviations on either side of the mean once the sensitivity is factored in. Thereafter, filtering is often used to better identify true defects.

In one embodiment, defect sensitivity is basically a user defined multiple of the standard deviation. Through actual analysis of good and bad die, the user defines a multiple of the standard deviation that most accurately defines all of the defects yet does not wrongly define good die as defects. An example is as follows. Assume three known good die with gray scale values of 98, 100 and 102. The mean is 100 and the standard deviation is ±2. The user through inspection knowledge defines the defect sensitivity at 5. The upper and lower limits are then 110 and 90 respectively.

In one embodiment, the minimum defect contrast is similarly a user defined absolute limit. In the above example, the user through knowledge is aware that gray scale measurements with a minimum contrast of 15 are not defective. The minimum defect contrast is thus set at 15 and as a result the upper and lower limit must be 115 and 85 instead.

In the preferred embodiment, a test image is created using simple image subtraction after each pixel of an unknown quality wafer or die is viewed. A test image is created by basically subtracting the gray scale measurement of the test pixel, for example 98, from the good die upper limit, for example 110, for that pixel, or subtracting the good die lower limit, for example 90, from the gray scale measurement of the test pixel, again 98, to get a binary good or bad indication. The upper and lower limits have preferably been sensitized. If the number is positive then it is colored black as being inside the range (or alternatively white), and if the number is negative then it is colored white as being outside of the range (or alternatively black). A binary black and white image results. This image allows for filtering at a much more rapid speed due to its simplicity in comparison to saving an actual 256 color image. Alternatively, a full color, such as 256 color, image may be used if sufficient memory is available and optimal speed is not vital.

In one embodiment, one or more of the following filters are used on the binary black and white image. Image processing functions such as connection factoring and reduction factoring may then individually or all together be used. Statistical or data filtering on blob identification may also be performed individually or all together.

Connection factoring involves a "close" operation. The identified pixels, in the above example the white one, are dilated and then eroded, or double dilated and then eroded, or any other known combination. This connects or fills in the defects so as to filter out small defects or acceptable irregularities.

Reduction factoring involves an "open" operation. The identified pixels are eroded and then dilated, or double eroded and then double dilated, or any other known combination. This reduces noise.

Blob analysis involves identifying blobs on the binary black and white image. Once identified, various parameters of each are identified including, for example, size such as x size and y size, location, area, etc. Statistical or data filtering is then performed on the parameters of the blobs.

Such statistical or data filtering includes area filtering, size filtering, region of interest filtering, and interactive defect classification filtering. Area filtering discards blobs of a pre-set area or smaller. Size filtering discards blobs of a pre-set x or y size or smaller. Region of interest filtering allows the user to define locations on the die that are not of as much or any importance and as such any defects thereon would be irrelevant. Finally, interactive defect classification involves clustering of close but not touching identified pixels where the distance defining close is user defined.

Basically, the unknown quality die are inspected by viewing the image and comparing each pixel with its mean and standard deviation via the upper and lower limit values. Sensitivity and filtering also allows for compensation for factors that are deemed by the user to be more or less critical. In sum, if any one of the given viewed pixels in the unknown quality die is outside of the upper and lower limit values as sensitized and filtered, then the die is defective and as described below, that defective spot is inked or otherwise noted.

The step C8 is creating a defect map of the wafer W which is a collection of all of the defect data of all of the die and is stored in a data file. In the preferred embodiment, it is a binary black and white image.

As an alternative to the above described inspection steps, the alternative step C6 which is the step of collecting an image of the wafer W using the camera 20 by continuously moving the plate 12 so as to scan over all of the die on the wafer whereby the wafer is illuminated by a strobe light at a sequence correlating to the speed of the moving plate so that each die is strobed at the precise time it is under the camera 20. Basically a short illumination pulse of light on the moving plate effectively Freezes the image. This allows for the continuous collecting of images without necessitating the stop and go procedure of aligning the camera with a first die, viewing and recording that die, moving the plate 12 to align the camera with another die, viewing and recording this another die, and repeating these steps until all of the die on the wafer have been viewed and recorded, etc.

The overall defect review step D is generally at the conclusion of defect inspection on a given wafer W since it is at this point that defect classification is often desired. The defect inspection or detection process of steps C is all automatic and rapid whereby once complete the user may manually inspect only the defects found based upon the parameters, filters, sensitivities, etc., rather than all of the die or wafer for defects. Significant time is saved.

The step D1 is loading the defect map created in step C9. The step D2 is selecting a defect to review (or alternatively reviewing all of the defects on the wafer in order). The step D3 is moving the plate 12 so as to position the wafer W such that the particular defect is properly positioned under the camera 26. The step D4 is user viewing and classifying of the defect such that user of the system 10 views and classifies the viewed defect. Any number of classifications are available and the classifications are user defined. The step D5 is repeating of steps D2-D4 until all of the defects have been reviewed and classified. The step D6 is saving of classified defect map as well as alternatively or additionally saving the defect information in any of a number of other formats for database or other management and review.

The overall defect reporting step E is exporting or printing out the data stored in database format. This data may then be analyzed or otherwise used to perform statistical or other analysis on the types of defects, frequency of defects, location of defects, etc., which is useful to the wafer W manufacturers so as to allow them to focus on defect laden areas. This step E provides for complete and effective data analysis as it reports data in multiple formats including graphical, tabular, and actual image displays. The data that is placed in tabular format allows numerical values to be readily correlated with other values such as electrical formats. The graphical data representation quickly shows trends that would otherwise be difficult to see.

The system 10 is based upon standard computer technology such as Pentium®. Pro or similar computer platforms which allow for many different communication options of for example both a serial and network format. For instance, the system includes TCP/IP configuration and may alternatively include SEC-II/GEM or other computer industry standard protocols.

The system 10 may also be used to perform an inspection using a drift map. This is useful where the individual die of the wafer W are cut up on a film and stretched as needed for picking up and removal therefrom as is well known in the art. The problem here is that during stretching, the orthogonality may be lost and the die move in different directions and ways as the film material unevenly stretches. The approximately square or rectangular cut dies are now oriented in all different directions and as such a row of die is no longer straight but rather wavy or otherwise disoriented. When this drastic stretching and loss of orthogonality occurs, a drift map and drift step is added to account for this. This step is typically inserted prior to scanning.

In one embodiment, a frame grid is created for the purpose of defining the expected location of each die. It is known to stretch the film sawn wafers are transported on so as to allow easier picking up of each die without damaging neighbor die. This stretching however is typically not uniform resulting in disoriented die. The drift map predicts the stretched location of each die using the starting point of the die which was known due to the rigidity before sawing, and the pitch.

To create a drift map, a mark or dummy die is placed on the wafer at every nth location, such as every $10^{th}$. Using machine vision, the system 10 looks for the mark at its expected location and then looks therearound if not found. Once the actual location is found, the machine vision proceeds to the expected location of the next mark and reiterates through the process. Once all of the marks have been found, a pitch is calculated assuming consistent behavior in between marks. Using this pitch and knowing the original location of each die prior to sawing, a drift map is created which accurately predicts the location of the die.

The system 10 may also incorporate use of an autofocus feature. Such a feature is based upon a sharpness calculation where a sweep of the image is taken at each of a predefined picture point. Thereafter, a sharpness calculation is used to find the correct focus point. To save time, this may be performed on only every nth image.

In sum, the basic sequence of operation is as follows, with the automated wafer transfer and wafer mapping options removed. The operator or user must first train the system as to what a "good die" is, that is create a good die model, or choose an existing good die model. As indicated above, this involves inputting and using location markers to properly align a plurality of known good die such that each die is imaged from the exact same x, y, z and θ location. In addition, wafer and/or die geometry, sizes, pitch, number of rows, number of columns, etc., must be inputted prior to imaging of good die. The plurality of good die are then each aligned and viewed by the CCD camera such that the computer system then forms a "good die" model by grouping all of the common characteristics, noting the ranges of pitches, colors, angles, locations, etc. Basically, the system 10 performs wafer inspection by studying a user provided set of known good die. It is generally preferred that at least twenty or thirty die are provided, although no minimum or maximum is required. Inspection parameters are also set to indicate how close an unknown quality die must match specific characteristics of the "good die" model to be considered a good die. These include sensitivity parameters and defect filters.

The user must also create or select a previously stored inspection recipe. This includes information as to how wafers W are selected from cassettes or other storage receptacles, how the dies on each wafer W are to be selected for defect inspection, how defect inspection map files are imported and exported, etc.

The system 10 is now ready to inspect unknown quality die. If identification codes are being used as are necessary where wafer mapping is active, one must be inputted at this point. Thereafter, a wafer W (or sawn wafer, or die in gel-pak, or die in waffle pak, etc.) is loaded onto the inspection area and specifically the wafer test plate 12 (which is under the inspection camera). This is accomplished using the wafer providing means 14. Thereafter, the wafer alignment device 16 aligns the wafer at the same x, y, z, and θ location as the "good die" were loaded by using the defined and/or trained alignment features and parameters of step A1. The magnification desired is then selected and thereafter the camera 20 is focused.

The system is now ready to collect an image of the selected area (the first die position) of the wafer W using the camera 20 by moving the plate 12 to align the camera with the selected area, such as a first die position, so as to take a first image thereof which may be the whole wafer, a part of the wafer, a die, or a part of a die and then viewing and recording that image. Automatic defect inspection and bond pad analysis are performed on the die's digital image. If the die is inked, it is automatically identified (mapped) as an "inked die", and typically not inspected. If the die is not inked, and a defect was found, then the system will collect and store detailed information about each defect such as defect location on the die, size, shape, etc.

The plate 12 is then moved to align the camera with another selected area, which may be the next adjacent area or not, to take an image hereof (the second die position) on the wafer adjacent to the first image. Basically, the plate is indexed under the inspection camera to the next die position. This second die position is then viewed and recorded. These steps are repeated until all of the images on the wafer have been viewed and recorded. Simultaneous with these image viewing steps, defect sensitivity and filtering are used in conjunction with the "good die" model viewing to determine if initial anomalies or differences between the "good die" model and the image are actual defects or if they should be filtered out. A defect map of the wafer W is then created in the computer system from the collection of all of the defect of all of the die including all of the defects found thereon.

In another embodiment, rather than move the plate in incremental steps, the plate is continuously moved during strobe illumination thereof. The sections of the wafer are then scanned by synchronizing the camera with a strobe illumination so that when the camera is properly positioned over each section of the moving substrate, the strobe illumination occurs simultaneous with the image collection via the camera.

At the conclusion of defect inspection on a given wafer W, defect classification is often desired. Each archived defect is manually reviewed by the user where the plate 12 is moved to the position on the wafer W that the particular defect is positioned at so that the user may view and classify the defect. This is then repeated for all defects. The classified defects are then saved as a classified defect map.

That wafer is then removed and another wafer is loaded for inspection. This removal and loading of a new is either manually performed or may be automatically performed.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

Although the present disclosure has been described with reference to preferred embodiments, workers skilled in the art will recognize that changes can be made in form and detail without departing from the spirit and scope of the present disclosure.

What is claimed is:

1. An automated defect inspection system, comprising:
   a visual inspection device for visual inputting of a plurality of first die positions having a user defined level of quality during training and for visual inputting of a plurality of unknown quality die positions for inspection;
   an illuminator for providing short pulses of light to each of the unknown quality die positions at a rate that is correlated with a rate at which the unknown quality die positions are aligned with the visual inspection device during movement relative to the visual inspection device to effectively freeze motion of the unknown quality die positions for visual inputting by the visual inspection device; and
   a computer system having processing and memory capabilities for developing a model of the plurality of first die positions having the user defined level of quality and comparing the unknown quality die positions to the model to identify defects.

2. The automated defect inspection system of claim 1, wherein the plurality of first die positions comprises a substrate selected from a group consisting of a whole patterned wafer, a sawn patterned wafer, a broken patterned wafer, at least one portion of a patterned wafer, an individual die, at least one portion of an individual die, a plurality of individual die, at least one portion of a plurality of individual die, multiple die in a waffle pak, a multi-chip module (MCM), a JEDEC tray, and an Auer boat.

3. The automated defect inspection system of claim 1, wherein the plurality of first die positions comprises an entire die sawn from a wafer.

4. The automated defect inspection system of claim 3, wherein the entire die sawn from the wafer is mounted on a film frame.

5. The automated defect inspection system of claim 1, wherein the plurality of first die positions comprises a selected portion of a die sawn from a wafer.

6. The automated defect inspection system of claim 5, wherein the die sawn from the wafer is mounted on a film frame.

7. The automated defect inspection system of claim 1, wherein the illuminator is at least one of a brightfield illuminator positioned approximately above, a darkfield illuminator positioned approximately above, and a darkfield laser positioned approximately about a periphery of a boundary defining the plurality of first die positions.

8. The automated defect inspection system of claim 1, wherein a number of the plurality of first die positions having the user defined level of quality that is visually inputted during developing of the model is numerically sufficient to compute a mean and a standard deviation.

9. The automated defect inspection system of claim 8, wherein the number of the plurality of first die positions used for the model is at least twenty.

10. The automated defect inspection system claim 8, wherein the number of the plurality of first die positions used for the model is at least thirty.

11. The automated defect inspection system claim 8, wherein the number of the plurality of first die positions used for the model is at least 100.

* * * * *